United States Patent [19]

Aggarwal

[11] Patent Number: 4,920,196
[45] Date of Patent: Apr. 24, 1990

[54] HUMAN LYMPHOTOXIN

[75] Inventor: Bharat B. Aggarwal, San Mateo, Calif.

[73] Assignee: Genentech, Inc., South San Francisco, Calif.

[21] Appl. No.: 11,448

[22] Filed: Feb. 6, 1987

Related U.S. Application Data

[63] Continuation of Ser. No. 608,316, May 7, 1984, abandoned, which is a continuation-in-part of Ser. No. 403,671, Jul. 30, 1982, abandoned.

[51] Int. Cl.$^5$ .................... C07G 7/00; A61K 45/05; C12N 5/00
[52] U.S. Cl. ................... 530/351; 530/412; 530/415; 530/416; 530/417; 530/418; 530/419; 530/422; 530/827; 424/85.1; 514/2; 514/8; 514/21; 435/70.2; 435/70.4; 435/240.1; 435/240.2
[58] Field of Search ............... 530/351, 412, 415, 416, 530/417, 418, 422, 827; 435/68, 70, 240.1, 240.2; 424/85.1; 514/2, 8, 21

[56] References Cited

U.S. PATENT DOCUMENTS

| | | |
|---|---|---|
| 4,309,418 | 1/1982 | Green .................................. 514/21 |
| 4,405,601 | 9/1983 | McEntire et al. ................... 424/95 |
| 4,457,916 | 7/1984 | Hayashi et al. ..................... 424/101 |
| 4,481,137 | 11/1984 | Ohnishi et al. ...................... 530/351 |
| 4,708,948 | 11/1987 | Iwata et al. .......................... 530/351 |
| 4,752,575 | 6/1988 | Granger et al. ..................... 530/351 |
| 4,785,077 | 11/1988 | Kornbluth ............................ 435/68 |

FOREIGN PATENT DOCUMENTS

| | | |
|---|---|---|
| 0090892 | 10/1983 | European Pat. Off. . |
| 0131789 | 1/1985 | European Pat. Off. . |
| 0132125 | 1/1985 | European Pat. Off. . |
| 2106117 | 4/1983 | United Kingdom . |

OTHER PUBLICATIONS

Harris et al., *J. Immunol.*, 126(6), 1981, pp. 2165-2170.
Klostergaard et al., *Mol. Immunol.*, 18(12), 1981, p. 1049.
Klostergaard et al., *Mol. Immunol.*, 18(5), 1981, p. 455.
Pitchyangkul et al., *J. Chem. Hematology and Oncol.*, 11(4), 1981, p. 109.
Walker et al., *J. Immunol.*, 109(46), 1972, Cytotoxic Activity of Lymphocytes, p. 1233.
Klostergaard et al., *Mol. Immunol.*, 18(12), 1981, Purification of . . . Lymphotoxins to Electrophoretic Homogeneity, p. 1049.
Klostergaard et al., *Mol. Immunol.*, 18(5), 1981, Human Lymphocytes, p. 455.
Pitchyangkul et al., *J. Clin. Hematology and Oncology*, 11(4), 1981, Purification of Lymphotoxin . . . Supernate, p. 109.
Fuhrer et al., *J. Chromat.* 248, 1981, Rapid Separation . . . HPLC, p. 427.
Fuhrer et al., Inter. Symposium on HPLC of Proteins and Peptides, 1981, p. 11.
The Human LT Serum X, the Initial Form Released by T-Enriched . . . M. W. Classes, *J. Immunol* 125(6), 1981, p. 2165.
Armstrong et al., "J.N.C.I.", 74(1): 1-9 (Jan. 1985).
Flick et al., "Biological Response Modifiers", P. F. Torrence, Ed. 171-218 (1985).
Oettgen et al., Recent Results Cancer Res., 75: 207-212 (1980).
Matthews et al., Br. J. Cancer 42: 416-422 (1980.

(List continued on next page.)

*Primary Examiner*—Garnette D. Draper
*Attorney, Agent, or Firm*—Max D. Hensley; Carolyn R. Adler

[57] ABSTRACT

Biologically active lymphotoxin polypeptide species, and derivatives, fragments, aggregates and pharmaceutically acceptable salts are provided. The lymphotoxins are substantially homogenous, and are formulated into pharmaceutical compositions. The lymphotoxins are purified to a specific activity of at least $10^6$ units/mg protein by using hydrophobic substances and/or immobilized lentil lectin, or with the use of other chromatographic processes such as ion exchange chromatography, HPLC or gel filtration.

28 Claims, 14 Drawing Sheets

```
                                                                    NH2-His(
                                                                         (Ser
NH2-Leu Pro Gly Val Gly Leu Thr Pro Ser Ala Ala Gln Thr Ala Arg Gln His Pro Lys Met His Leu Ala His(
                  5               10                15                20                    25

Thr Leu Lys Pro Ala Ala His Leu Ile Gly Asp Pro Ser Lys Gln Asn Ser Leu Leu Trp Arg Ala Asn Thr Asp
                        30              35              40                    45      CHO           50
                                                  CHO
      Arg Ala Phe Leu Gln Asp Gly Phe Ser Leu Ser Asn Asn Ser Leu Leu Val Pro Thr Ser Gly Ile Tyr Phe Val
                      55              60              65                    70                      75

Tyr Ser Gln Val Val Phe Ser Gly Lys Ala Tyr Ser Pro Lys Ala Thr Ser Ser Pro Leu Tyr Leu Ala His Glu
                      80              85              90                    95                     100

. Val Gln Leu Phe Ser Ser Gln Tyr Pro Phe His Val Pro Leu Leu Ser Ser Gln Lys Met Val Tyr Pro Gly Leu
                     105             110             115                   120                     125

Gln Glu Pro Trp Leu His Ser Met Tyr His Gly Ala Ala Phe Gln Leu Thr Gln Gly Asp Gln Leu Ser Thr His
                     130             135             140                   145                     150

Thr Asp Gly Ile Pro His Leu Val Leu Ser Pro Ser Thr Val Phe Phe Gly Ala Phe Ala Leu-COOH
                     155             160             165                   170
```

OTHER PUBLICATIONS

Hiserodt et al., J. Immun. 119, 374–380 (1977).
Karpas, Br. J. Cancer 36: 437–445 (1977).
Rubin et al., Proc. Natl. Acad. Sci., U.S.A., 82: 6637–6641 (1985).
Karpas, Nature 313: 636 (1985).
Neumann et al., Biochem. J. 194: 847–856 (1981).
Pharmacia Catalog, pp. 52–61 (Aug. 1983).
Kull et al., "J. of Immunology", 126(4): 1279–1283, (Apr. 1981).
Ruff et al., "Infection and Immunity", 31(1): 380–385 (Jan. 1981).
Reidarson et al., "J.N.C.I.", 69(4): 879–887 (Oct. 1982).
Kull et al., "P.N.A.S., U.S.A.", 81: 7932–7936 (Dec. 1984).
Granger et al., "Human Lymphokines", Khan, A. & Hill, N., Ed. 495–507 (Rec'd Aug. 1982) (Pub. Jun. 30, 1982).
Wright et al., "J. of Immunology", 126(4): 1516–1521 (Apr. 1981).
Williamson et al., "P.N.A.S., U.S.A.", 80: 5397–5401 (Sep. 1983).
Papermaster et al., "Cancer", 45: 1248–1253 (Mar. 1980).
Kunitomi et al., "Am. J. of Pathology", 80(2): 249–260 (Aug. 1975).
Bloom, B. & Glade, P. ed. "In Vitro Methods in Cell-Mediated Immunity", Academic Press, 200–201 (1971).
Gately et al., "Cellular Immunology", 27: 82–93 (1976).
Granger et al., "Cellular Immunology", 38: 388–402 (1978).
Gately et al., "Prog. Allergy", 25: 106–162 (1978).
Toth et al., "Molecular Immunology", 16: 671–679 (1979).
Lee et al., "Cellular Immunology", 48: 166–181 (1979).
Klostergaard et al., "Molecular Immunology", 17: 613–623 (1980).
Granger et al., "Cellular Responses to Molecular Modulators", Miami Winter Sym. 18: 287–310 (Jan. 1981).
Watson et al., "Lymphokines", 6: 95–116 (1982).
Proctor et al., "Clinical Research", 30(1): 55A (1982).
Parr et al., "Br. J. Cancer", 48: 395–403 (1983).
Wallach et al., "The Biology of the Interferon System", DeMaeyer & Schellekens, Ed., 293–302 (Sep. 1983).
Devlin et al., "Cellular Immunology", 88(2): 297–308 (1984).
Evans, "Cancer Immunol. Immunother", 12: 181–190 (Apr. 1982).
Johnson et al., "Molecular Immunology", 20(11): 1241–1244 (1983).
Russell et al., "J. of Immunology", 109(4): 784–790 (Oct. 1972).
Fair et al., "Molecular Immunology", 16: 185–192 (1979).
Pichyangkul et al., "Human Lymphokines", 173–183 (Rec'Aug. 82) (1982), Kahn & Hill Ed. (Pub. Jun. 30, 1982).
Yamamoto et al., "J. of Biological Response Modifiers", 3: 76–87 (1984).
Powell et al., "Lymphokine Research", 4(1): 13–25 (1985).
Aksamit et al., "J. of Immunology", 122(5): 1785–1790 (May 1979).
Papermaster et al., "Cellular Responses to Molecular-Modulators", Miami Winter Symposia-18: 271–283 (Jan. 1981).
Gray et al., "Nature", 312: 721–724 (Dec. 1984).
Pennica et al., "Nature", 312: 724–729 (Dec. 1984).
Stone-Wolff et al., "J. Exp. Med.", 159: 828–843 (Mar. 1984).
Aggarwal et al., Presentation made at the 3rd Int. Lymphokine Workshop in Haverford, Pa., Aug. 1–5, 1982.
Aggarwal et al., Presentation made at the 3rd Int. Symp. on Thymic Hormones & Lymphokines, Washington, D.C., May 31–Jun. 3, 1983 and Abstract of the Presentation available on May 31, 1983.
Harris et al., "J. of Immunology", 126(6): 2165–2170 (Jun. 1981).
Orr et al., "Lymphokine Research", 3(4): 264 (summer 1984).

PARTIAL AMINO ACID SEQUENCE OF HUMAN LYMPHOTOXIN

Tryptic Fragment $T_2$ (5K)

```
                         5                              10
      Ala - Thr - Ser - Ser - Pro - Leu - Tyr - Leu - Ala - Cys -
                              15                              20
    - Glu - Val - Gln - Leu - Phe - Cys - Cys - Gln - Tyr - Pro -
                         25
    - Phe - X - Val - X - X - . . . . . . . . .
```

Tryptic Fragment $T_1$ (15K)

```
                         5                              10
      His - Ser - Thr - Leu - Lys - Pro - Ala - Ala - His - Leu -
      (Ser)        (Leu) (Lys) (Pro) (Ala)
      (Ala)
                              15                              20
    - Ile - Gly - Asp - Pro - Ser - Lys - Gln - Asn - (Cys) - Leu -
                              25                              30
    - Leu - Trp - Arg - Ala - Asn - (Ser) - Asp - Arg - Ala - Phe -
                              35                              40
    - Leu - Glu - (Ser) - Gly - Phe - Ser - Leu - Asp - X - Asn -
                                         (Cys)        (Thr)   (Thr)
                                         (Phe)        (Ser)   (Ser)
                                                      (His)   (His)
                                                      (Arg)   (Arg)
                                                      (Cys)   (Cys)
                         45
    - Val - Leu - X - X - X -
      (Asn) (Val)
```

```
NH2-Leu Pro Gly Val Gly Leu Thr Pro Ser Ala Ala Gln Thr Ala Arg Gln His Pro Lys Met His Leu Ala His{ NH2-His{
            5                          10                       15                      20          {Ser
                                                                                                     25

Thr Leu Lys Pro Ala Ala His Leu Ile Gly Asp Pro Ser Lys Gln Asn Ser Leu Leu Trp Arg Ala Asn Thr Asp
                30                       35                      40              CHO   45          50

Arg Ala Phe Leu Gln Asp Gly Phe Ser Leu Ser Asn Asn Ser Leu Leu Val Pro Thr Ser Gly Ile Tyr Phe Val
                55            CHO        60                      65                      70          75

Tyr Ser Gln Val Val Phe Ser Gly Lys Ala Tyr Ser Pro Lys Ala Thr Ser Ser Pro Leu Tyr Leu Ala His Glu
                80                       85                      90                      95         100

Val Gln Leu Phe Ser Ser Gln Tyr Pro Phe His Val Pro Leu Leu Ser Ser Gln Lys Met Val Tyr Pro Gly Leu
               105                      110                     115                     120         125

Gln Glu Pro Trp Leu His Ser Met Tyr His Gly Ala Ala Phe Gln Leu Thr Gln Gly Asp Gln Leu Ser Thr His
               130                      135                     140                     145         150

Thr Asp Gly Ile Pro His Leu Val Leu Ser Pro Ser Thr Val Phe Phe Gly Ala Phe Ala Leu-COOH
               155                      160                     165                     170
```

HUMAN LYMPHOTOXIN

This is a continuation of application Ser. No. 608,316, filed May 7, 1984, now abandoned, which is a continuation-in-part of U.S. Ser. No. 06/403,671 filed July 30, 1982 now abandoned.

BACKGROUND OF THE INVENTION

The invention herein concerns lymphokines, a class of proteins originally extracted in impure form from lymphocytes, and believed to have anti-tumor activity. Specifically, the invention concerns a homogeneous preparation of the human lymphokine, lymphotoxin, and a process for preparing it.

Lymphokines are biologically active, hormone-like peptides or proteins produced by stimulated lymphocytes. The properties and functions of these lymphokines, including those exhibiting cytotoxic activity, have been studied extensively. Lymphotoxin is a type of lymphokine which is produced not only by mitogen or antigen stimulated lymphocytes, but also by cell lines which are grown in tissue culture derived therefrom.

Lymphotoxin has been implicated in the regulation of the immne system (1) and has been reported to inhibit tumor cell growth both in vivo (2–7) and in vitro (8–10). Under in vitro conditions, it is a more potent inhibitor of tumor cells than of normal ones from the same species (11–15). Also, lymphotoxin preparations have been shown to inhibit UV or chemical carcinogen induced cell transformations (16–17). The in vitro activity of lymphotoxin may be assayed by a number of methods as will be set forth hereinbelow and these methods provide convenient means for following the processes of purification of lymphotoxin from crude extracts. In vivo studies in human beings have also shown that crude preparations of lymphotoxin are effective in tumor regression (5,7).

Previous studies have been conducted with relatively impure fractions of cell supernatants prepared from lymphocytes or cell lines derived therefrom. A number of laboratories have attempted to prepare lymphotoxin in purified form, without conspicuous success (18–24). The present invention uniquely provides a homogeneous preparation of lymphotoxin proteins useful as an anti-tumor agents in mammals.

SUMMARY OF THE INVENTION

In one aspect, the invention is directed to lymphotoxin per se and its natural and otherwise equivalent pharmaceutically acceptable salts and pharmaceutically acceptable derivatives, including fragments thereof, in substantially homogeneous form. Homogeneity is defined in its classical sense including the substantial absence of other proteins of human origin. However, homogeneous lymphotoxin includes various species or derivatives of lymphotoxin such as lymphotoxin aggregates, lymphotoxin fragments as well as mixtures of such fragments and aggregates. Further, lymphotoxin and its fragments are characterized by their C-Terminal amino acid sequence, whereas various lymphotoxin species are characterized by different N-Terminal sequences. In an embodiment substantially homogeneous lymphotoxin is provided in nonaggregated form. The entire mature amino acid sequence for lymphotoxin, as well as a biologically active fragment thereof, is disclosed.

The invention further concerns pharmaceutical compositions containing the aforesaid lymphotoxin, and methods of using same for administration as an antitumor agent.

In still another aspect, the invention concerns processes for preparing homogeneous lymphotoxin. In particular, the process comprises contacting a nongelatinous hydrophobic substance and/or immobilized lentil lectin with an admixture of lymphotoxin and other protein to adsorb lymphotoxin, followed by elution of the lymphotoxin from the substance or lentil lectin.

BRIEF DESCRIPTION OF THE DRAWINGS

FIG. 12 shows the results of amino acid sequencing of the fragments from trypsin-digest of the purified N-terminal histidine species of lymphotoxin. Those residues which are in parentheses are alternatives or uncertain determinations.

FIG. 13 is a diagrammatic representation of the amino acid sequencing strategy for determining the amino acid sequence of lymphotoxin.

FIG. 14 is the amino acid sequence for two lymphotoxin species, one of which commences with an N-terminal leucine and another of which begins with N-terminal histidine.

DETAILED DESCRIPTION

A. Definitions and Abbreviations

Figure 1:
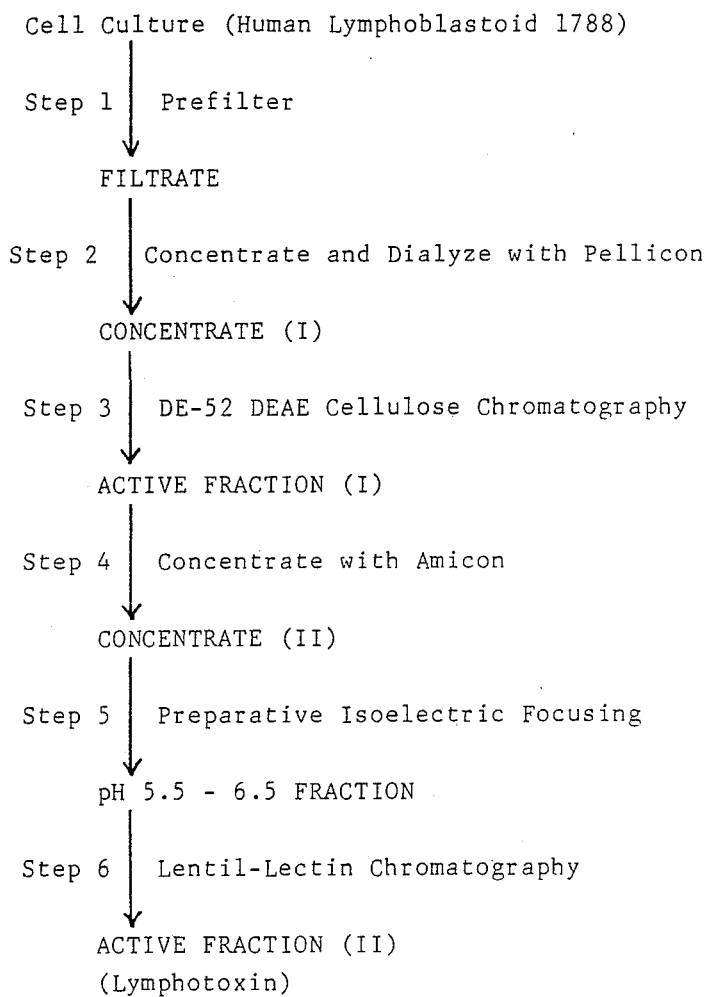
FIG. 1 is a schematic representation of a preferred embodiment of the purification of lymphotoxin as practiced by the invention.

The sequence of amino acids in lymphotoxin will be designated by using the standard IUPAC three letter abbreviations for amino acid "residues". "Residue" has a functional meaning within the amino acid sequence. In the body of the sequence the residue and the abbreviation therefor denotes the amino acid less one N-hydrogen and the —OH from the carboxyl; at a terminal position, the designation denotes this residue with the appropriate hydrogen or hydroxide. Thus, in the sequence, $Ala_1-Ala_2-Ala_3$,

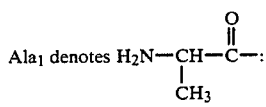

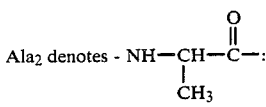

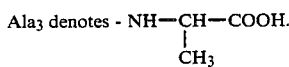

All chiral amino acid residues herein are of the natural or L-configuration unless otherwise noted. All peptide sequences are written according to the convention whereby the N-terminal acid is on the left, and the C-terminal on the right.

"Lymphotoxin" means polypeptides having detectable Specific Activity as defined below which contain regions homologous with the polypeptides set forth in FIG. 14. Thus, lymphotoxin as defined herein includes the two species in FIG. 14, hydrolytic fragments thereof, aggregates (including trimers) of such species with one another, and salts and derivatives of such species, all of which must exhibit detectable Specific Activity in order to fall within the scope of the term "lymphotoxin" as used herein.

"Peptide" and "protein" are used interchangeably herein to denote amino acid polymers; the conventional size distinctions wherein proteins are large and peptides small is not made, in view of the difficulty of finding agreement as to the boundary between the two.

"Amino acid residue" in general refers to a residue as defined hereinabove which is derived from one of the twenty amino acids coded for in proteins. This residue may however be modified so as to form a derivative as defined below.

As used herein the term "salts" refers to both salts of carboxyl groups of the polypeptide chain and to acid addition salts of amino groups of the polypeptide chain.

Salts of a carboxyl group may be formed with either inorganic or organic bases by means known in the art per se. Inorganic salts include, for example, sodium, calcium, ammonium, ferric or zinc, salts, and the like. Salts with organic bases include those formed, for example, with amines, such as triethanolamine, arginine or lysine, piperidine, caffeine, procaine, and the like.

Acid addition salts include, for example, salts with mineral acids such as, for example, hydrochloric acid, or sulfuric acid, and salts with organic acids such as, for example, acetic acid, or oxalic acid.

Derivatives may also be prepared from the functional groups which occur as side chains on the residues or the N- or C-terminal groups, by means known in the art, and are included in the invention as long as they remain pharmaceutically acceptable (as defined below). These derivatives may, for example, include:

aliphatic esters of the carboxyl groups;

amides of the carboxyl groups by reaction with ammonia, or with primary or secondary amines;

N-acyl derivatives which are derivatives of an amino group of the polypeptide formed with acyl moieties (e.g. alkanoyl or carboxyclic aroyl groups);

or O-acyl derivatives which are derivatives of a hydroxyl group (for example that of seryl or threonyl residues) formed with acyl moieties.

Both the salts and the derivatives encompassed by this invention are those which are "pharmaceutically acceptable" i.e., which do not destroy the activity of the lymphotoxin and which do not confer toxic properties on compositions containing them.

A number of abbreviations with respect to techniques also will be used, which are well known to those skilled in the art. Specifically, "DEAE cellulose chromatograph" refers to chromatography using diethylaminoethyl cellulose, which provides an ion exchange support for packing into chromatography columns. At high pH values, the column is an anion exchanger and negative residues stick to column. Elution can be accomplished either by lowering the pH, or, more preferably, with a salt gradient at constant pH.

"PAGE" is electrophoresis as performed on a polyacrylamide gel and separates proteins or peptides on the basis of charge. If sodium dodecyl sulfate (SDS) is incorporated into the gel (SDS-PAGE), the surface active nature of SDS results in a uniform negative charge on the peptide or protein which is a function of size. The result is that separation is based on the molecular size. Native-PAGE denotes the employment of this technique without the presence of SDS and thus, proteins are separated on the basis of charge.

"Isoelectric focusing" can be performed as a form of native PAGE wherein a pH gradient is maintained across the electrodes, causing each protein to stop, or "focus" at its isoelectric point. However, other supports, preferably, for example, dextran, typically Ultrodex-LKB are also practical.

Other chromatography supports are also available which are of particular interest for this invention. A lectin isolated from lentils, "lentil lectin" is capable of retaining, selectively, glycoproteins which have galactosyl and mannosyl residues. Elution is accomplished by providing a sugar solution; in the case of this particular support, the solution must be of mannose or galactose.

Under suitable circumstances, chromatographic procedures may be carried out preferably in a narrow bore column containing a fine particle resin under increased pressure to enhance the effectiveness of separation, i.e., by high pressure liquid chromatography (HPLC).

Concentration and salt removal are commonly used precursors to certain chromatographic or separation techniques employed in the invention. Salt removal may be performed by, for example, dialysis or gel filtration, or by a relatively recently developed technique, controlled pore glass (CPG).

A number of gel filtration and concentration techniques are also used. Certain commercially available materials are especially useful. "Pellicon" membrane is a sheet like material composed of polysulfone manufactured by Millipore, Inc. Bedford; and "Amicon" membrane is a similar material also composed of polysulfone and manufactured by Amicon. These materials are capable of retaining large molecules while permitting passage of smaller ones. They thus operate in the opposite way to molecular seives, which allow large molecules to pass readily but retard the passage of smaller ones. Both Pellicon and Amicon are useful as concentration tools, permitting the smaller molecules to be "filtered" away from the desired macromolecular structures.

The extent to which concentration of a solution to be chromatographed is desirable is largely a matter of practicability of application. Salt removal is necessary if ion exchange or other techniques which depend on total ionic strength are employed. These preparation methods and the extent to which they are required for particular separation procedures are well known in the art.

The cells used as the source of lymphotoxin in the present invention are lymphocytes or their transformants. The literature shows lymphotoxin to be present in preparations of "buffy coat white blood cells" converted by mineral oil induction; golden Syrian hamster or guinea pig peritoneal leukocytes (17) and lymphoblasts such as the human lymphoid cell lines RPMI 1788, B-21 and MOLT (25).

"Specific Activity" refers to the activity of the protein in standard lymphotoxin assays as related to the amount of protein by weight in the sample. As specified in the current disclosure, the activity of lymphotoxin is measured in terms of "units" which refer to the amount of lymphotoxin required to cause 50 percent lysis in target cells according to the assay procedure set forth hereinbelow. Several standard assay procedures are available. The assay procedure described herein in detail is based on ability to mediate lysis of mitomycin C-treated mouse fibroblast cells, as measured by staining capability.

An additional procedure involves the release of the tritium from tritiated thymidine labeled murine alpha-L-929-fibroblast cells, a lymphotoxin sensitive cell strain (26). The "units" used to define specific activity may differ depending on assay procedure as does the mg protein determined. "Specific Activity" as defined herein is units/mg protein, where "units" are measured by the assay set forth below, and mg protein is measured by the method of Bradford (infra).

"Impurities" as they pertain to the lymphotoxin prepared by the method of this invention refers to those substances associated with lymphotoxin in its normal cellular environment or in a crude extract, filtrate, or centrifugate.

The overall process for preparation of homogeneous lymphotoxin is summarized in FIG. 1. The specific method for preparation of the various lymphotoxin species differs somewhat. The following Examples B through F deal primarily with the preparation and characterization of lymphotoxin having an N-terminal histidine residue. The method for the N-terminal leucyl species is described in Example G.

B. Purification of Lymphotoxin-Embodiment I (1) Tissue Culture and Harvest

The human lymphoblastoid cell line RPMI 1788 was obtained from ATCC (No. CCL 156) and the seed culture was grown in 400 ml of the medium RPMI-1640, obtained from Irvine Scientific, Santa Ana, Calif., containing 10 mM HEPES and 5% fetal calf serum innoculated at a cell density of $6 \times 10^4$ cells/ml with 400 mls in 2 liter roller bottles. After 5 days at 37° C., when culture reaches a cell density of $2 \times 10^6$ ml, the cells were harvested and washed 2 times with a serum-free culture medium RPMI-1640. The cells were then transferred into a serum-free medium RPMI-1640 containing 10 mM HEPES and one percent Penicillin-Streptomycin at a cell density of $5 \times 10^5$ cells/ml. (The absence of serum in this medium is helpful in the purification of lymphotoxin, as the amount of contaminating protein is decreased). 400 ml of this cell suspension was placed in 2 liter roller bottles and also in 15 liter and 10 liter spinner flasks (Belco Glass Co., Vineland, N.J.), which were substituted for 2 liter roller bottles in some instances. After 65 hours the culture medium was harvested for the lymphotoxin activity.

The cell suspensions from both roller bottles and spinner flasks were pooled. The cells from this pool were removed by passing through a 3 uM Sealkleen filter supplied by Pall Trinity Micro Corp., Cortland, N.Y. (Step 1 of FIG. 1). The clear filtrate was further concentrated and dialyzed, as follows (Step 2).

(2) Concentration and Dialysis of Filtrates

The filtrates were concentrated approximately 20 fold at 4° C. on a Pellicon membrane (supplied by Millipore Company) with a molecular weight cut-off of 10,000. The concentrated samples were further dialyzed against 5 mM phosphate buffer, pH 7.8 using the same Pellicon, set up in its dialysis mode. When the conductivity of the sample reached that of the dialysis buffer, the Pellicon membrane was rinsed thoroughly with the buffer and all the protein recovered.

The resulting concentrate was assayed for lymphotoxin activity as were the resultants from Steps 3 through 6, in order to determine specific activity. The specific activity of the concentrate (I) FIG. 1 in a typical run was found to be of the order 2,000–3,000 units per mg of protein. Chromatography on a Sephacryl S-300 column to determine molecular size gave a single peak of activity at approximately 70,000 daltons.

(3) DEAE Cellulose Chromatography

The concentrate (I) was subjected to DEAE cellulose chromatography on a DEAE-52 cellulose column equilibrated in 5 mM phosphate buffer pH 7.8 (Step 3). After the sample was loaded, the column was washed with the equilibration buffer and thereafter it was eluted with a 0–0.3M linear sodium chloride gradient.

Figure 2:
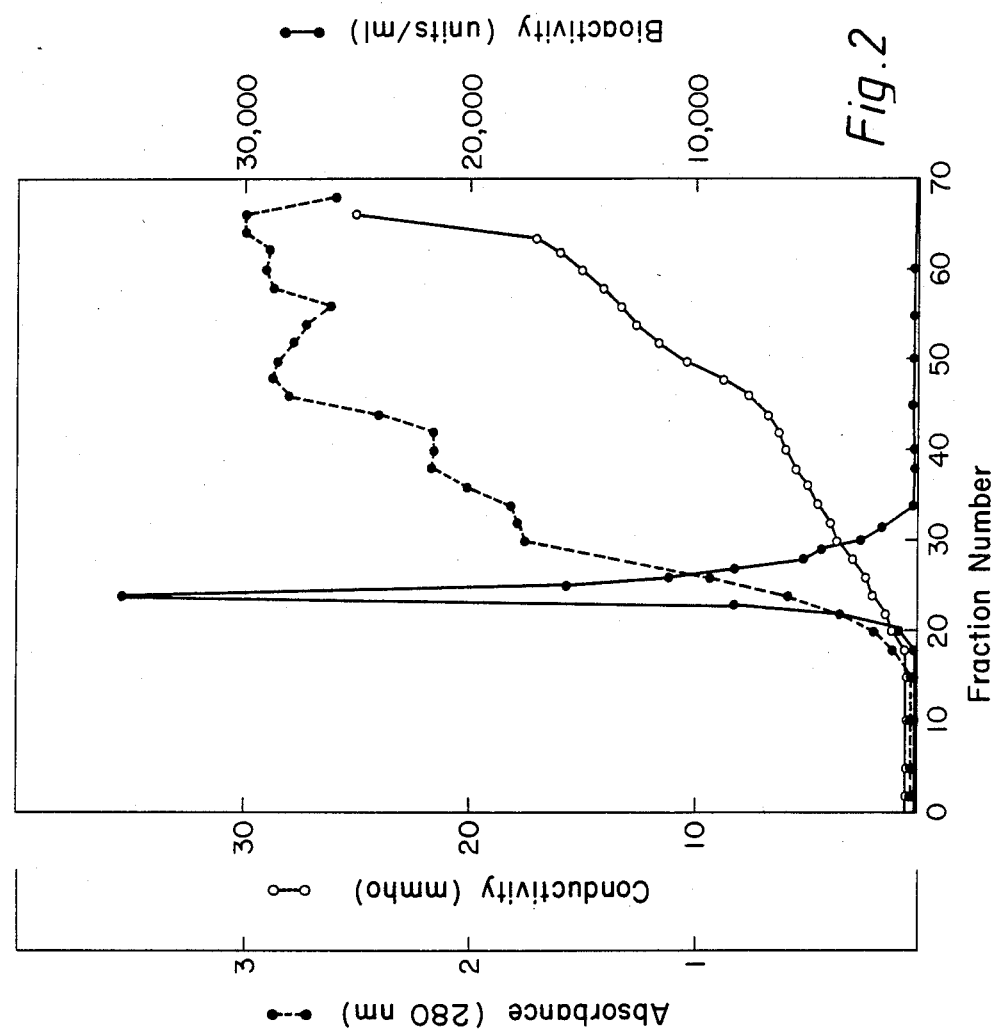
FIG. 2 shows the elution pattern fromm a DEAE cellulose purification step, specifically elution from DE-52 using 0–0.3M NaCl gradient. The activity elutes at approximately 0.1M, while large amounts of protein are retained.

The active fraction was identified by selecting the fraction of the highest specific activity as defined above. A single sharp peak of activity eluted at around 0.1M NaCl as shown in FIG. 2. Typically, this active fraction (I) of FIG. 1 would have a specific activity of the order of 20,000–30,000 units per mg protein, a 10 fold purification.

(4) Isoelectric Focusing

The active fraction is then concentrated using an Amicon stir cell with 10,000 (PM-10) molecular weight cut-off membrane, (Step 4 of FIG. 1).

The concentrate (II) was dialyzed against 2.5 mM Tris and 20 mM glycine pH 8.2 and run on a dextran flat bed (Ultrodex-LKB) containing Ampholine carrier ampholytes in the pH range 5–8 (Step 5). The basic apparatus used for preparative isoelectric focusing was that supplied by LKB (2117 Multiphor). The sample was mixed with the whole gel bed before the pH gradient was formed. After placing the electrode strips on either side of the gel bed, the electrofocusing was run along its length with a constant power of 8W for 15-20 hours at 8° C. The focused zones were collected by sectioning the gel bed with a fractionating grid and then removing each section with a spatula. Elution of the protein from the respective gel section was achieved in several small disposable columns using 50 mM ammonium bicarbonate. The absorbance at 280 nm, lymphotoxin activity, and the pH of the eluted fractions were determined.

Figure 3:
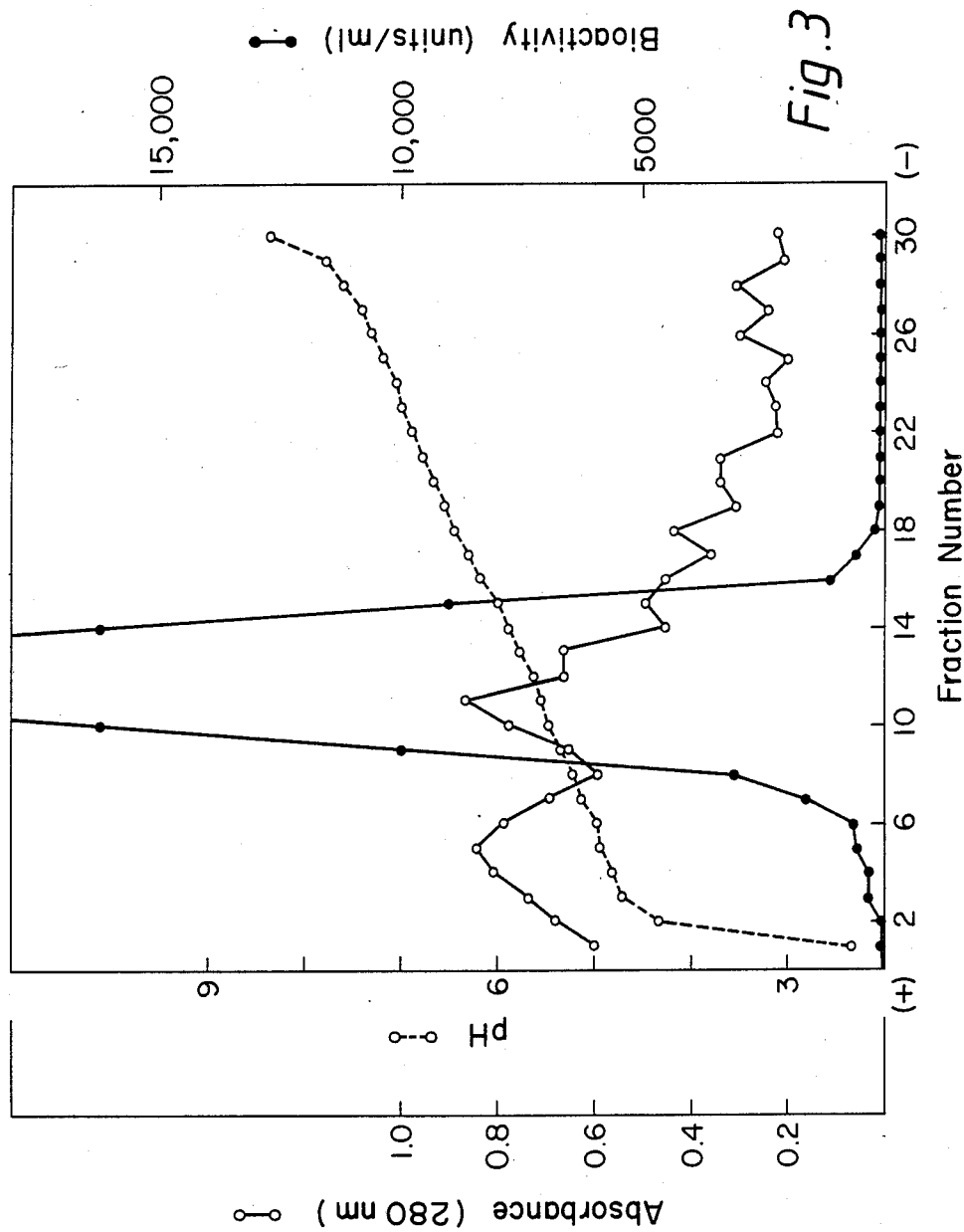
FIG. 3 is the isoelectric focusing pattern obtained in a typical preparation, showing activity, protein and pH pattern.

FIG. 3 shows the activity, protein and pH profile obtained. Though proteins were spread in the whole gel bed, more protein contaminants are observed in the acidic region as compared to basic pH range. The lymphotoxin activity was spread through the pH range of 5.5 to 6.5. Due to the presence of Ampholines it was difficult to determine accurately the protein concentration of the active fraction, thus it was not possible to calculate the degree of purification obtained at the isoelectric focusing step. The recovery of activity from this step was, however, fairly quantitative.

(5) Lentil Lectin Chromatography

Figure 4:
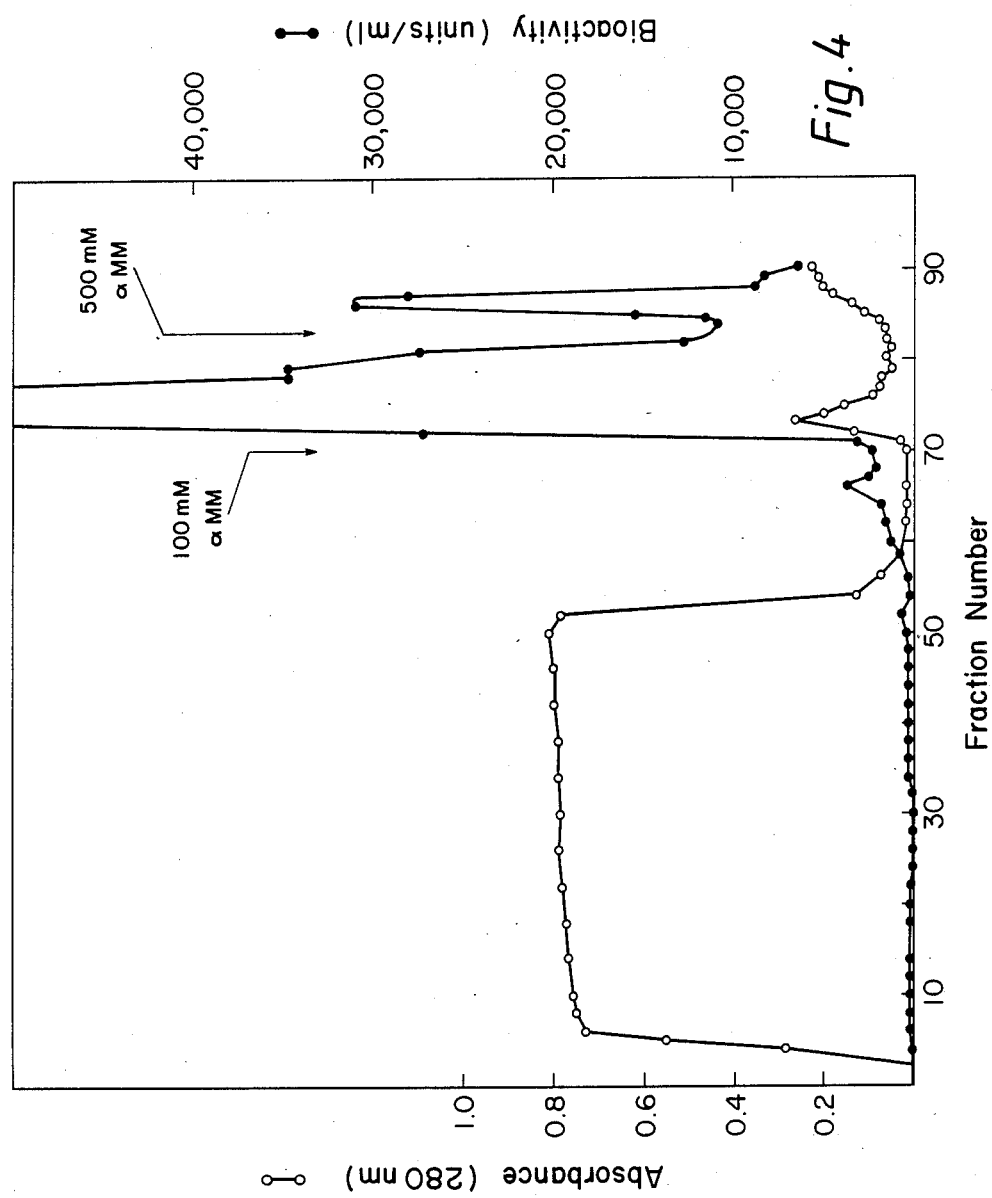
FIG. 4 is the elution pattern from a lentil lectin sepharose purification step. More than 95% of the total protein with no lymphotoxin activity is filtered through the column prior to the elution of the lymphotoxin.

The pool of the isoelectric focusing eluates containing lymphotoxin activity was applied on a Lentil Lectin (Pharmacia) column equilibrated in 10 mM phosphate buffer pH 7.8 (Step 6). After loading the sample the column was washed with the equilibration buffer and then eluted with 50 mM or 100 mM alpha-methylmannoside solution prepared in 10 mM phosphate buffer. The results are shown in FIG. 4. More than 95% of the protein, lacking in lymphotoxin activity, filtered through the column initially, and washing with column equilibration buffer (10 mM phosphate buffer pH 7.8) also did not elute the activity. When the column was exposed to 50-100 mM alpha-methylmannoside, a large peak of activity eluted with very little protein. The recovery of units of activity in this step was greater than 90 percent. The active fraction had specific activity on the order of 10 to 100 million units per mg.

C. Characterization of Purified Lymphotoxin

The active fraction eluted from the Lentil Lectin column was further subjected to the following analytical techniques and has the following properties:

(1) Gel Filtration

Figure 5:
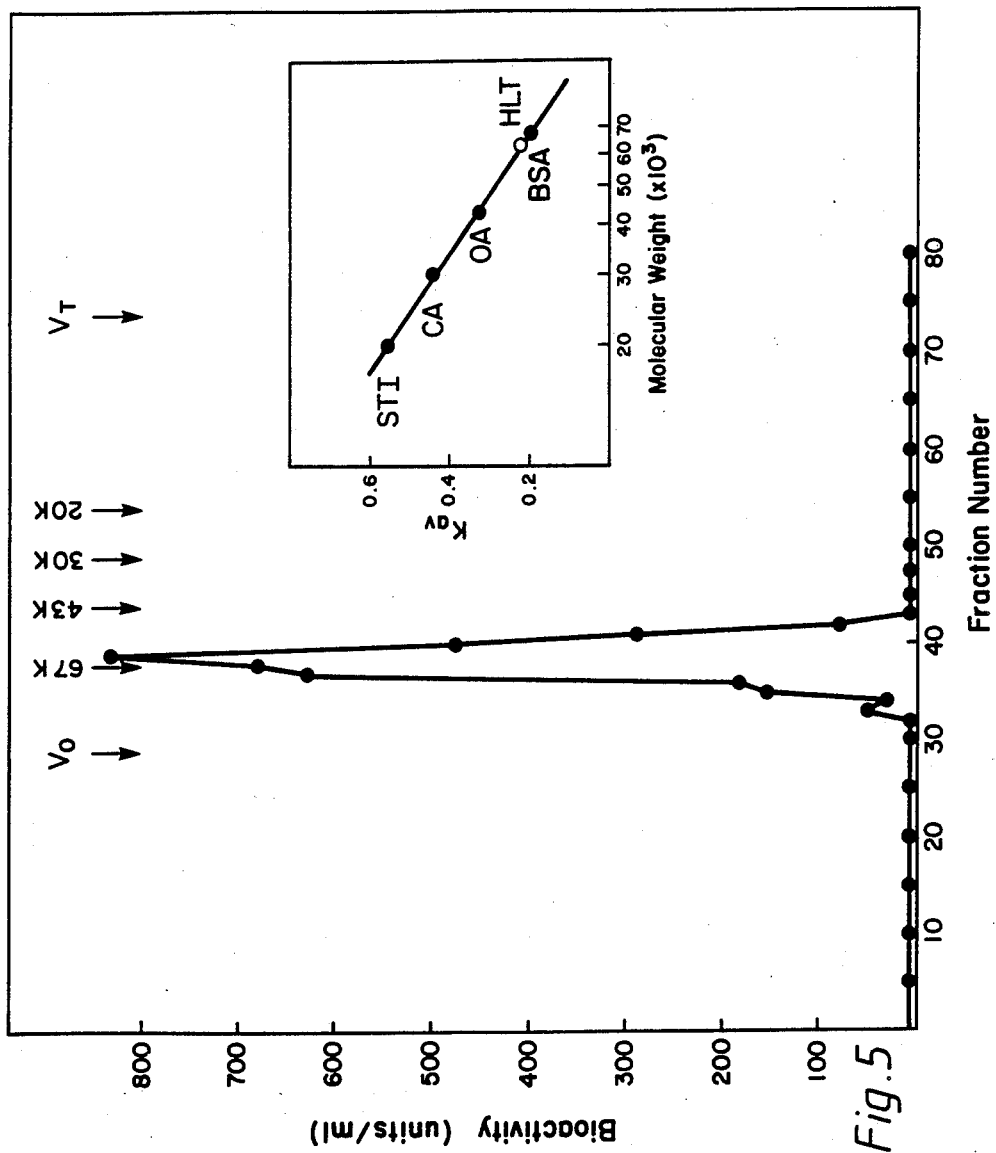
FIG. 5 depicts the elution profile of a lymphotoxin activity from Sephadex G-100. The insert shows the calibration curve for molecular size, using the known molecular weight proteins: soybean trypsin inhibitor, carbonic anhydrase, ovalbumin, bovine serum, and albumin. Blue dextran is used to determine a size maximum.

Gel permeation chromatography gave a single peak at 64,000 daltons, (as shown in FIG. 5). The active fraction from the lentil lectin column was applied to a Sephadex G-100 column (Pharmacia Fine Chemicals, Piscataway, N.J.), previously equilibrated with the eluting solvent, 10 mM phosphate buffer containing 0.5M in NaCl. The elution pattern was calibrated with bovine serum albumin, ovalbumin, carbonic anhydrase and soybean trypsin inhibitor; the elution of the lymphotoxin in the 64,000 dalton range indicates aggregation of individual peptides, as well be apparent from the results below.

(2) HPLC Chromatography

Figure 6:
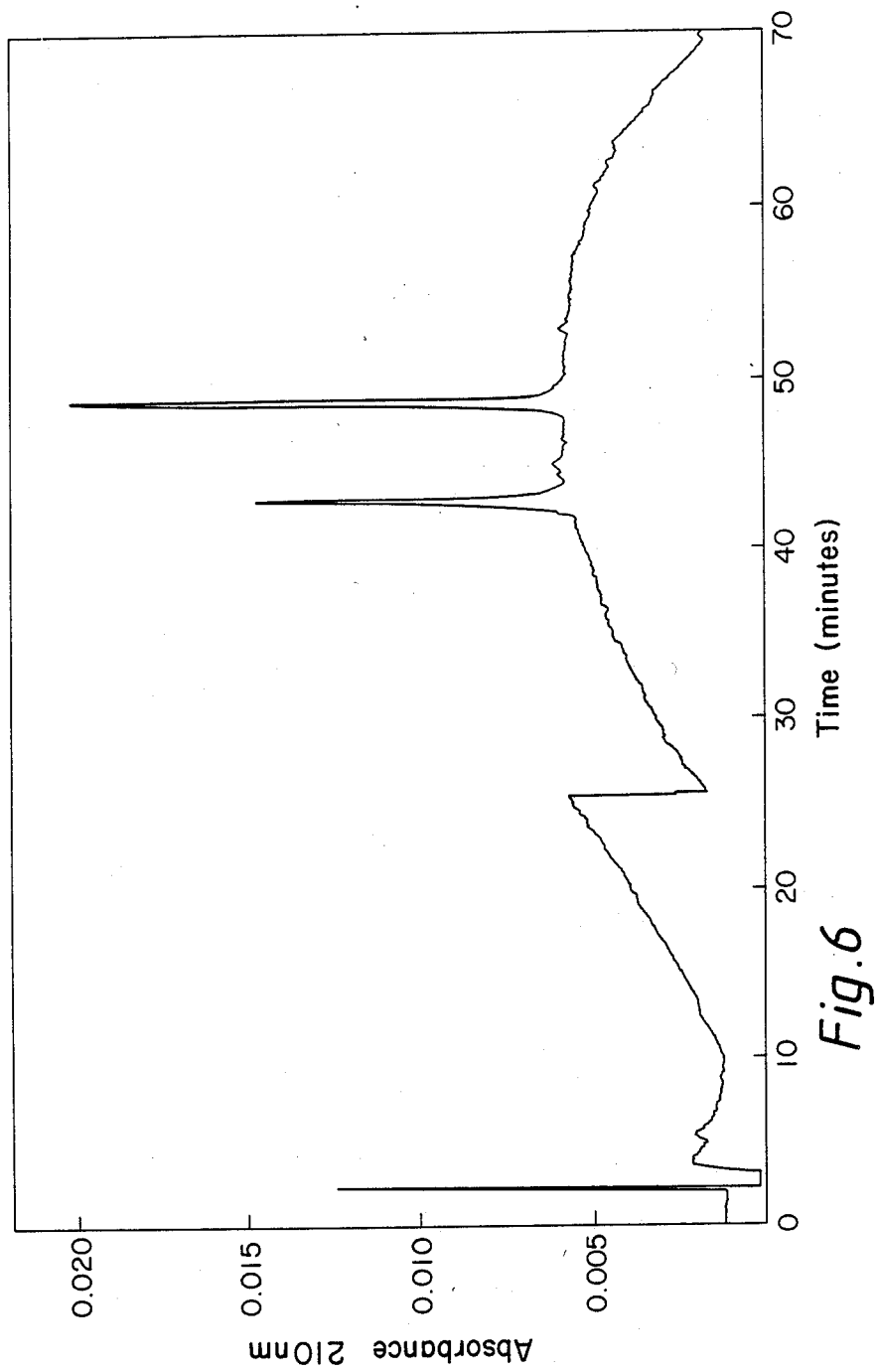
FIG. 6 shows the results of HPLC used to analyze a purified lymphotoxin fraction from the lentil lectin column.

HPLC chromatography showed a substantially homogeneous preparation, as shown in FIG. 6.

The active fraction from the Lentil Lectin column was concentrated on a Amicon stir cell using PM-10 membrane and applied on a Synchropak RP-P column (25 cm×4.1 mm, Synchrom, Inc., Linden, Ind.). The effluent was monitored at 210 nm and at 280 nm absorbances using a Spectra Physics SP 8000 high pressure liquid chromatograph. The elution conditions consisted of a linear gradient from 0.1% trifluoroacetic acid to 70% acetonitrile in 0.1% trifluoroacetic acid at 25° C. and a flow rate of one ml per minute. A major protein peak which elutes at a concentration of about 50% acetonitrile is obtained (FIG. 6) and when run on 12.5% SDS-PAGE, this fraction contains protein with a molecular weight of 20,000. Besides this 20K peak on HPLC, there were also minor peaks which eluted at 43% and 51% acetonitrile with molecular weights of 15K and 70K respectively. The HPLC solvents appear to inactivate the lymphotoxin molecule, thus it was not possible to determine the activity of the 20,000 molecular weight band.

(3) SDS-PAGE

Figure 7:
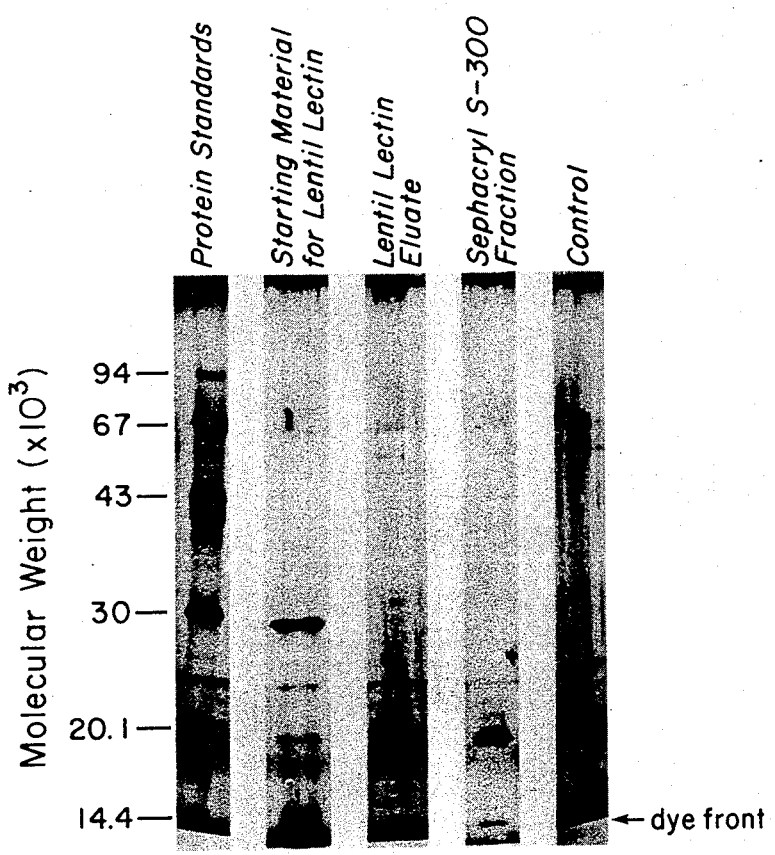
FIG. 7 is the size distribution of a lentil lectin active fraction as determined by SDS-PAGE. A standard using the 20K fraction from the gel filtration step of FIG. 5 is also shown.
Figure 8:
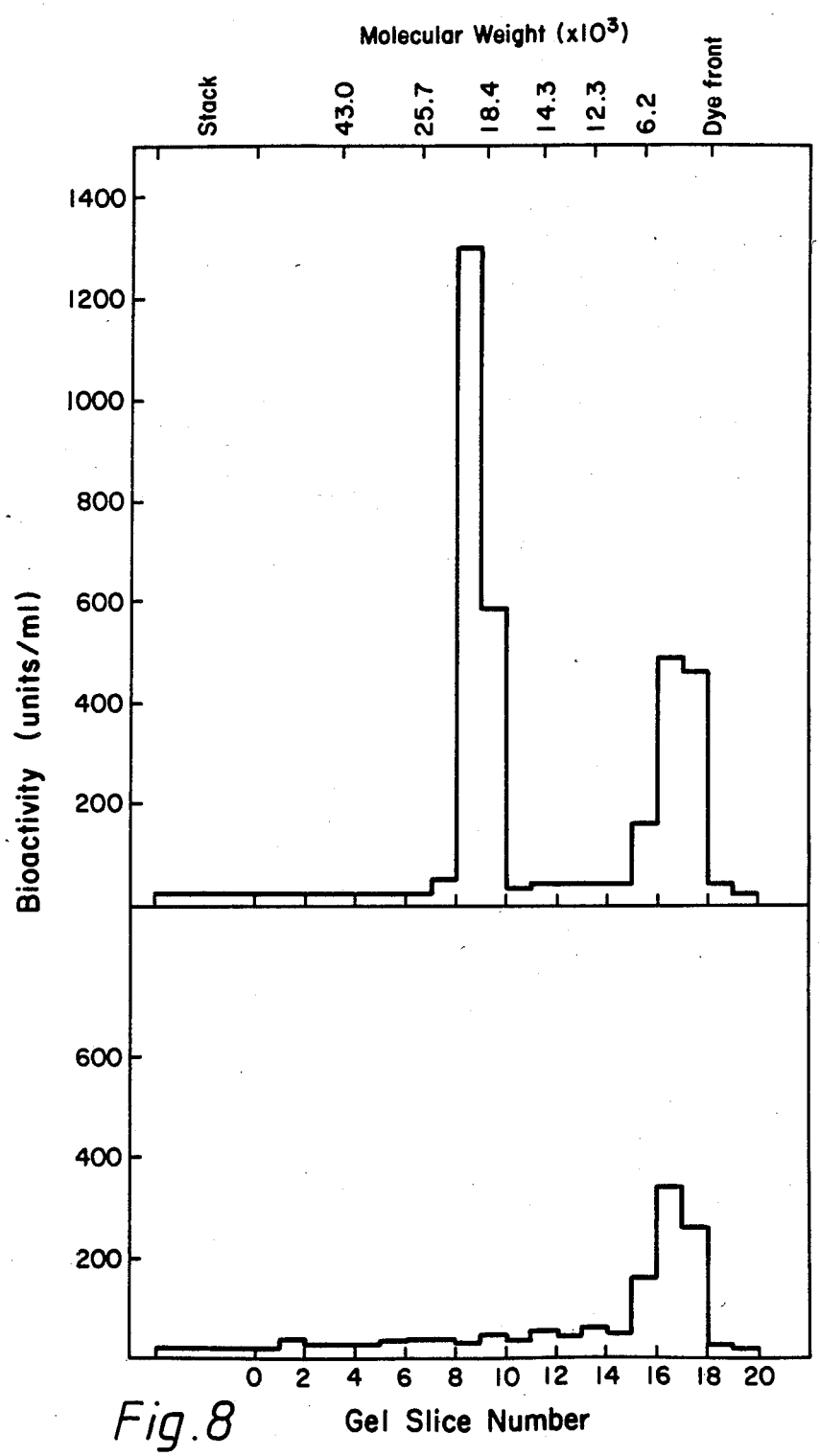
FIG. 8 is the elution profile of a lymphotoxin activity from SDS-PAGE. The upper panel shows the results using the gel in column C of FIG. 7. The lower panel is a control using only buffer (column E of FIG. 7). Slight activity appears to be an artifact associated with the dye front.

SDS-PAGE showed the majority of the protein to conform to a size estimate of approximately 20,000 daltons (FIG. 7). The lymphotoxin activity was associated with this 20,000 dalton fraction, as shown in FIG. 8. The SDS-PAGE was performed according to the method of Laemmli, et al. (27), which is incorporated herein by reference, using resolving acrylamide gel concentration of 12.5-15%.

(4) Native-PAGE

Native-PAGE also gave a peak of approximate MW of 20,000, as subsequently determined by SDS-PAGE.

The active fraction from the Lentil Lectin column was subjected to the native-PAGE procedure of Laemmli, et al. (27) with slight modifications. Both preparative (1.5-4 mm thick) and analytical (0.75 mm thick) gels consisted of 7.5% acrylamide for resolving gel and 4% for stacking gel. The running buffer used in both cases was Tris 25 mM pH 6.8. The analytical gel was run at constant current of 22 mA and preparative gel was run at 100 mA keeping the temperature constant.

Figure 9:
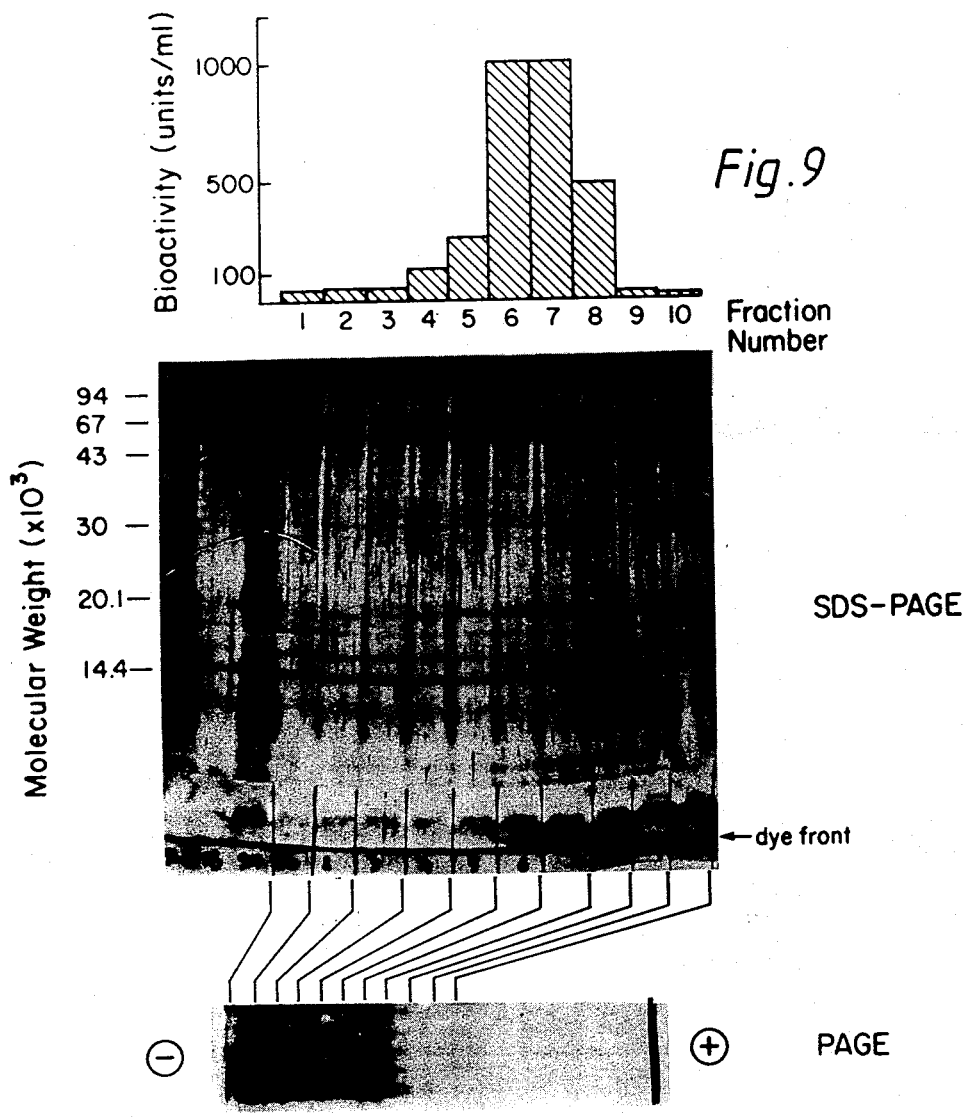
FIG. 9 shows an analysis of the Rf 0.33 fraction obtained by native-Page on a purified lymphotoxin by activity determination and by SDS-PAGE. This figure confirms a 20,000 MW at Rf 0.33 on native-PAGE. The lowest panel shows the origin of the gel slices from native-PAGE run on the purified lymphotoxin. These slices were assayed both for activity (upper panel) and size (middle panel).

At the end of the electrophoretic run, the protein on the gel was visualized by silver staining (28) incorporated herein by reference, to give a diffused band of Rf of 0.33. FIG. 9 gives a more detailed explanation of these results -as there shown, it was determined in a separate experiment that when gels are sliced and eluted by incubating the slices overnight at 4° C. in 50 mM ammonium carbonate buffer from the native-PAGE, the lymphotoxin activity is associated with a gel slice of Rf 0.33. The eluates from these gel slices were applied on SDS-PAGE, and the 20,000 MW band appeared only in those eluates which had lymphotoxin activity.

(5) Analysis by Tryptic Digestion and Isolation of Peptides

The purified lymphotoxin preparation was digested with trypsin-TPCK (Worthington) using 1 part trypsin, 20 parts protein in 50 mM ammonium bicarbonate buffer pH 8 for 24 hours at room temperature. The fragments have approximate molecular weights of 15,000 and 5,000.

Figure 10:
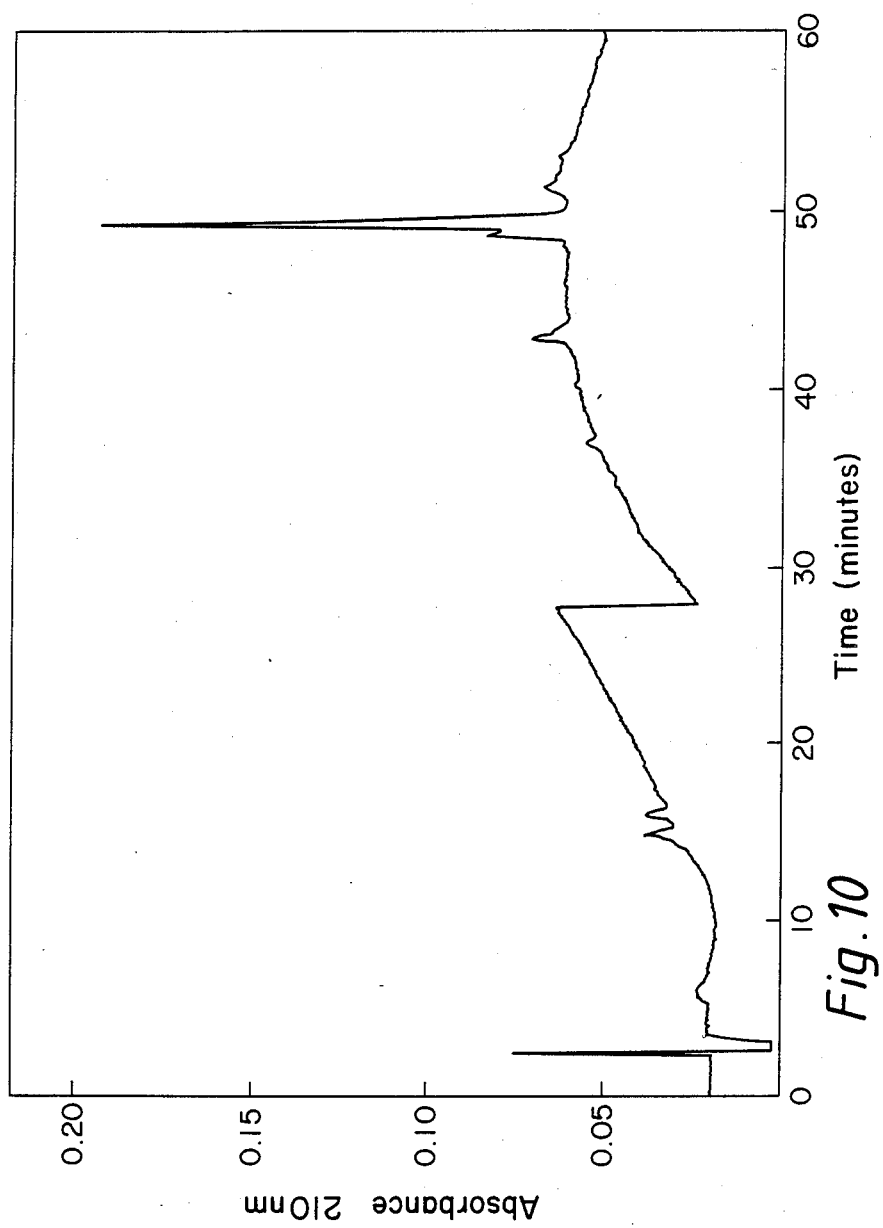
FIG. 10 is the elution pattern from HPLC of a tryptic digest of a homogenous lymphotoxin.
Figure 11:
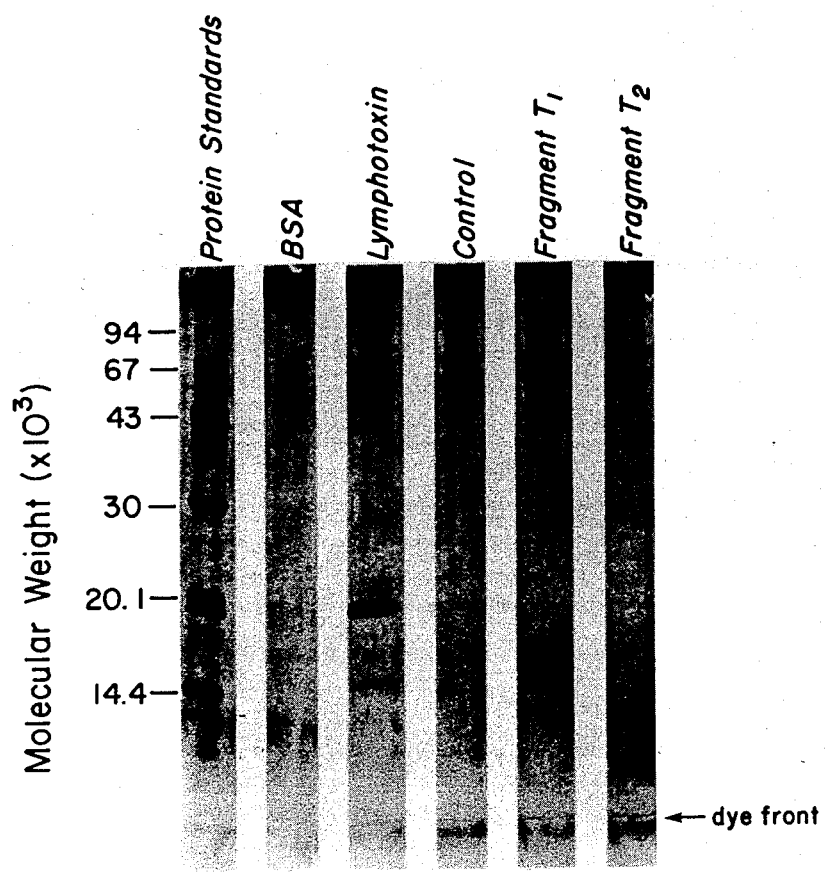
FIG. 11 is the SDS-PAGE molecular weight analysis on the $T_1$ and $T_2$ fractions shown in FIG. 10.

At the end of hydrolysis, the tryptic peptides were chromatographed by HPLC on a Lichrosorb RP-18 column (25 cm×4.6 mm, EM reagents, Cincinnati, Ohio) at 25° C., using Spectra Physics SP-8000 chromatograph. The peaks were detected at 210 nm and 280 nm after elution with a linear gradient of 0.1% trifluoroacetic acid to 50% acetonitrile in 0.1% trifluoroacetic acid at a flow rate of two ml per minute. (For later amino acid sequence analysis, each peak was collected, lyophilized and stored at −20° C.). As shown in FIG. 10, two peaks, T-1 and T-2, were observed eluting at 42.3% and 48.4% acetonitrile concentration respectively. The molecular size of each of these 2 peaks as determined by SDS-PAGE (FIG. 11) was 15,000 for T-1 and 5,000 for T-2. Both at 210 nm and 280 nm, the T-2 peak with relatively lower MW had higher absorbance than the T-1 peak.

The completeness of the trypsin hydrolysis was confirmed by applying a small aliquot of the hydrolyzed preparation to SDS-PAGE and showing that 20,000 dalton band was undetectable, and had been replaced by the 15,000 and 5,000 dalton bands.

Furthermore, the composition formed by the trypsin digestion as herein described exhibits lymphotoxin activity.

(6) Automated Amino Acid Sequence Analysis

Both intact and tryptic fragments were sequenced by automatic amino acid sequencing techniques by suspending the samples in 0.6 ml of 0.2M acetic acid and transferring the suspension into the cup of a Beckman 890C sequencer which had been previously coated with 4 mg polybrene and 100 nmoles norleucine. The phenyl thiohydanation (PTH) amino acids were identified using an ultrasphere ODS (25 cm×4.6 mm, 5 μM) column at a flow rate of one ml per minute with a program as described in, Kohr, W. et al (29) incorporated herein by reference.

The results obtained with both the intact protein and the tryptic fragments are shown in FIG. 12. As there seen, certain positions in the sequence could not be identified with certainty. However, sufficient identification was made to show that the 15K fragment (T-1) corresponds to the N-terminal portion of the intact lymphotoxin.

The above example is intended to illustrate rather than limit the invention. Other cell lines can be used as starting material; and equivalent chromatographic methods employed. The greatest purification appears to be achieved by the use of lentil lectin chromatography and as long as this step is included, a variety of preliminary steps remain satisfactory. Lentil lectin has not heretofore been used in the isolation of lymphotoxin. However, the integrated process as shown above provides a result which is substantially a pure protein.

D. Assay Procedure for Lymphotoxin Activity

The activity of lymphotoxin during purification was monitored by the modified cell-lytic assay of Spofford (30) which is incorporated herein by reference. Briefly, mouse L-929 fibroblast cells were grown in microtiter plates in the presence of mitomycin C. After 12–18 hours 0.125 ml of serially diluted sample to be assayed for lymphotoxin is added to each well. After 48 hours, the plates were washed and the lysis of the cells induced by lymphotoxin was detected as adhering to the plates by staining the plates with a 1% solution of crystal violet in methanol:water (1:4 v/v). The intensity of stain was observed both visually as well as spectrophotometrically at absorbance of 450 nm and 570 nm transmission using a Dynatech spectrophotometer. The cells plated in a microtiter well with culture medium alone were set at 0% lysis whereas those with 3M guanidine hydrochloride solution provided an end point for 100% lysis. One unit of lymphotoxin is defined as the amount required for 50% cell lysis out of 12,000 cells plated in each well.

E. Determination of Protein

The protein concentration throughout purification was determined by the method of Bradford (31) incorporated herein by reference. Briefly, 0.8 ml of the sample to be assayed was mixed with the 0.2 ml of the reagent concentrate solution from Bio-Rad Labs, Richmond, Calif. The reaction mixture was read at 595 nm in a Perkin Elmer Spectrophotometer Model 55B. This assay was linear between 2–20 μg of bovine serum albumin. During the final stages of purification, a rough estimate of protein was also made either from absorbance at 280 and 206 nm or by the silver staining of the SDS-polyacrylamide gels. This rough estimate was eventually confirmed by the nanomoles of various amino acid residues appearing at each cycle of the protein sequencing.

F. Utility and Administration

Administration of the lymphotoxin or its salts or derivatives or its active components can be via any of the accepted modes of administraton for agents which exhibit anti-tumor activity. These methods include oral, parenteral or topical administrations and otherwise systemic forms. Local or intravenous injection is preferred. The active components, for example, include the tryptic digest of lymphotoxin which has been shown to be active, and there is no reason it could not be used as the active ingredient in a pharmaceutical composition of this kind and for this purpose.

Depending on the intended mode of administration, the compositions used may be in the form of solid, semisolid or liquid dosage forms, such as, for example, tablets, pills, capsules, powders, liquids, suspensions or the like, preferably in unit dosage forms suitable for single administration of precise dosages. The compositions will include a conventional pharmaceutical carrier or excipient the lymphotoxin or the pharmaceutically acceptable salts or derivatives thereof and, in addition, may include other medicinal agents, pharmaceuticals, agents, carriers, adjuvants, etc. Such excipients may include other proteins, such as, for example, human serum albumin or plasma preparations.

The amount of active compound administered will of course, be dependent on the subject being treated, the severity of the affliction, the manner of administration and the judgment of the prescribing physician. However, an effective dosage is in the range of 0.007–7 ng/kg/day, preferably 0.07–0.7 ng/kg/day. For solid compositions, conventional non-toxic solid carriers include, for example, pharmaceutical grades or mannitol, lactose starch, or magnesium stearate. Liquid pharmaceutically administerable compositions can, for example, be prepared by dissolving, dispersing, etc. the lymphotoxin as defined above and optional pharmaceutical adjuvants in a carrier, such as, for example, water, saline, aqueous dextrose, glycerol, ethanol, and the like, to thereby form a soluton or suspension. If desired, the pharmaceutical composition to be administered may also contain minor amounts of nontoxic auxiliary substances such as wetting or emulsifying agents, pH buffering agents and the like, for example, sodium acetate or sorbitan monolaurate. Actual methods of preparing such dosage forms are known, or will be apparent, to those skilled in this art; for example, see *Remington's Pharmaceutical Sciences,* Mack Publishing Company, Easton, Pa., 15th Edition, 1975. The composition or formulation to be administered will, in any event, contain a quantity of the lymphotoxin in an amount effective to alleviate the symptoms of the subject being treated.

G. Purification of Lymphotoxin-Embodiment II

The human lymphoblastoid cell line RPMI-1788 was grown in 15L spinner flasks to a cell density of $4\times10^5$ cells per ml using a serum free culture medium as described previously above. Lymphotoxin was induced 10–20 fold over basal levels by the inclusion of 20 ng/ml of phorbol myristate acetate in the serum free RPMI- 1640 medium. After 65 h of culture, the cells were harvested by filtration, and the lymphotoxin activity in the filtrate was absorbed to controlled pore glass beads (Electronucleonics) in a column (5 cm×20 cm), reequilibrated with 5 mM phosphate buffer (pH 7.4) and eluted with 50 percent ethylene glycol in 5 mM phosphate buffer (pH 7.4). Throughout the purification described in this Example G, 0.1 mM phenylmethyl sulfonyl fluoride (PMSF), a protease inhibitor, and 1 mM sodium azide, for inhibition of microbial growth, were included in all buffers. The eluate from glass beads contained 84,000 units of lymphotoxin/mg protein. This was followed by DEAE cellulose, Lentil Lectin Sepharose Chromatography, and preparative native PAGE as described above. Homogenity of the protein was determined by SDS-PAGE, reverse-phase HPLC on a LiChrosorb RP-18 column and by amino terminal sequencing, again substantially as set forth above.

The purification scheme of this example resulted in lymphotoxin yields of 20.1 percent based on the starting culture medium. The protein product was assayed at 40±15 million units of lymphotoxin/mg of protein. This lymphotoxin preparation contained greater than 95 percent by weight of a lymphotoxin species having N-Terminal leucine (FIG. 14) and an approximate molecular weight of 25,000 on SDS-PAGE. The theoreticl molecular weight of the protein component of the N-Terminal leucyl species is 18,664 daltons; the remaining approximately 6,500 daltons was attributed to a glycosyl side chain at Asn-62 (FIG. 14), and other O-linked sugar residues. The tissue culture supernatant contained putative trimers of this species (60,000 Da by TSK-HPLC or 64,000 Da by Sephadex G-100 chromatography). The isoelectric point was 5.8. Lymphotoxin lost about half of its control specific activity upon heating in aqueous solution for 60 min. at 60° C., and about 80 percent of its control specific activity at 80° C. for 5 min., as shown in the following table.

| TEMPERATURE (°C.) | TIME (Min) | BIOACTIVITY (Units) |
|---|---|---|
| Control | — | 233,100 |
| 60 | 5 | 259,700 |
| 60 | 15 | 588,000 |
| 60 | 30 | 334,100 |
| 60 | 60 | 125,370 |
| 80 | 5 | 33,190 |
| 100 | 5 | 360 |

Lymphotoxin (10 μg/ml) lost greater than about half of its specific activity at pH less than about 5 or greater than about 10 when stored for 24 hours at 4° C. in ammonium bicarbonate buffer; it was most stable at pH 8-9.

The remainder of the lymphotoxin mixture was the N-terminal histidyl species (FIG. 14) with a molecular weight of about 20,000 obtained in examples B-F above. The 25,000 Da species is full length mature lymphotoxin, while the 20,000 Da species is a fragment or "clip" believed to result from enzymatic hydrolysis during purification of the lymphotoxin. Both of these species exhibit the same specific activity, (within the variation imposed by the limits of the assay) and therefore are useful in the procedure of Example F.

Purified lymphotoxin exhibited tumor necrosis activity in vivo against Meth A sarcoma transplanted into (Balb/CXC57BC/b) F₁ mice and cytotoxic or cytostatic activity in virto on human tumor lines ME-180 (cervix cancer), SK-Br3 and MCF-7 (breast cancer), SK-CO-1 (colon cancer), and SK-OV3 (ovary cancer). Lymphotoxin also activated human polymorphonuclear neutrophils in vitro to express increased antibody-dependent cellular cytotoxicity, superoxide anion production and phagocytic ability.

The use of a hydrophobic solid or substance to adsorb lymphotoxin is novel and a considerable improvement in ease of use compared to the concentration and dialysis step of Example B. Flow rates are superior to gelatinous adsorbents such as sepharose; the preparation of the adsorbent is facile and its cost is low. Other hydrophobic solids besides silicates (glass), such as polyolefins (polyvinyl or polystyrene beads), are suitable for use as well.

Elution of lymphotoxin from such absorbents is readily affected by polar solvents having hydrophobic domains or aprotic solvents, examples besides ethylene glycol being low molecular weight polyethylene glycol or lower nontoxic alkanols (propanol or butanol). Such solvents also are useful in stabilizing the lymphotoxin molecule if carried through the purification procedure and present during storage and/or lyophilization of the product.

The cleavage techniques used in sequencing all of this protein (except the designated residues in the C-terminal region) are described as follows:

Trypsin Cleavage. Lymphotoxin was digested with trypsin in 0.1M ammonium bicarbonate buffer pH 8.0 at an enzyme to substrate ratio of 1:20 for 24 h at 25° C. The reaction was stopped by lyophilization.

Cyanogen Bromide Cleavage. Peptide T4 (1.0 nmole) was dissolved in 70 percent formic acid and a small crystal of CNBr was added. The solution was flushed with nitrogen and then was allowed to stand for 17 h at 25° C., guanidine hydrochloride was added to 4M final concentration and the mixture was applied directly to an HPLC column for separation of the cleavage products. No guanidine hydrochloride was added to the peptide extracted from the sequencer cup prior to CNBr cleavage.

Acetic Acid Cleavage. A 3.0 nmole sample of intact lymphotoxin or its peptides was dissolved in 0.2 ml of 10 percent acetic acid, and incubated at 110° C. for 2 h in a nitrogen atmosphere and then applied directly to an HPLC column for separation of cleavage products.

Lysine-C Protease Cleavage. 1.1 nmole of tryptic peptide T4 was digested with Lysine-C peptidase in 0.1M ammonium bicarbonate at 37° C. for 24 h at an enzyme to substrate ratio of 1:20 (w/w). Two equal additions of enzyme were made at zero time and at 6 h. The reaction was stopped by lyophilization and the cleavage products were separated by HPLC.

Chymotrypsin Cleavage. Cyanogen bromide peptide CN4 was dissolved in 300 μl of 0.1M ammonium bicarbonate, pH 8.9, and incubated with chymotrypsin at an enzyme to substrate ratio of 1:12.5 (w/w) at 37° C. for 24 h. Two equal additions of enzyme were made at time zero and 6 h. The sample was then applied directly to an RP4 column (Synchrom, Linden, IN) for isolation of cleavage products.

Purifications of Peptide. Peptides were purified by reverse-phase HPLC using C4 Synchropak and Lichrosorb RP-C18 columns on a Spectra Physics SP-8000 chromatograph system as described previously (W. Kohr et al, 1982, Anal. Biochem. 122: 348-359). Peaks were detected at 210 nm and at 280 nm after elution with a linear gradient of 1 to 70 percent acetonitrile or 1-propanol in 0.1 percent trifluoroacetic acid at a flow rate of one ml per minute. Isolated peptides were dried under vacuum, and then processed for amino acid analysis and sequencing.

Amino Acid Analysis. Peptides were hydrolyzed for 24 h and the intact protein was hydrolyzed for 24, 48 and 72 h with constant boiling HCl in evacuated sealed tubes at 110° C. The hydrolysates were dried down under vacuum using a Savant Speed-Vac concentrator and analyzed on a Beckman 6300 amino acid analyzer equipped with ninhydrin detector using a 45 minute automated program.

Carboxypeptidase Digestion: 1.0 nmol of CNBr peptide CN4 was dissolved in 200 μl of pyridine acetate, pH 5.5, and digested with 0.5 μg carboxypeptidase P. Norleucine was included as an internal standad and aliquots were removed at 0, 3, 30 and 120 minutes. The samples were analyzed for free amino acids after removing the peptide on a C18 Sep-Pak column (Waters Associates, Milford, Ma.). The data was calculated as moles of amino acids released per mole of protein digested.

Amino Acid Sequence Analysis. Sequential Edman degradation was performed with Beckman sequencer models 890B and 890C equipped with cold traps. Polybrene (1.25 mg) was used as a carrier in the cup. Each PTH amino acid was identified as previously described (Kohr et al, Id.).

Figure 13:
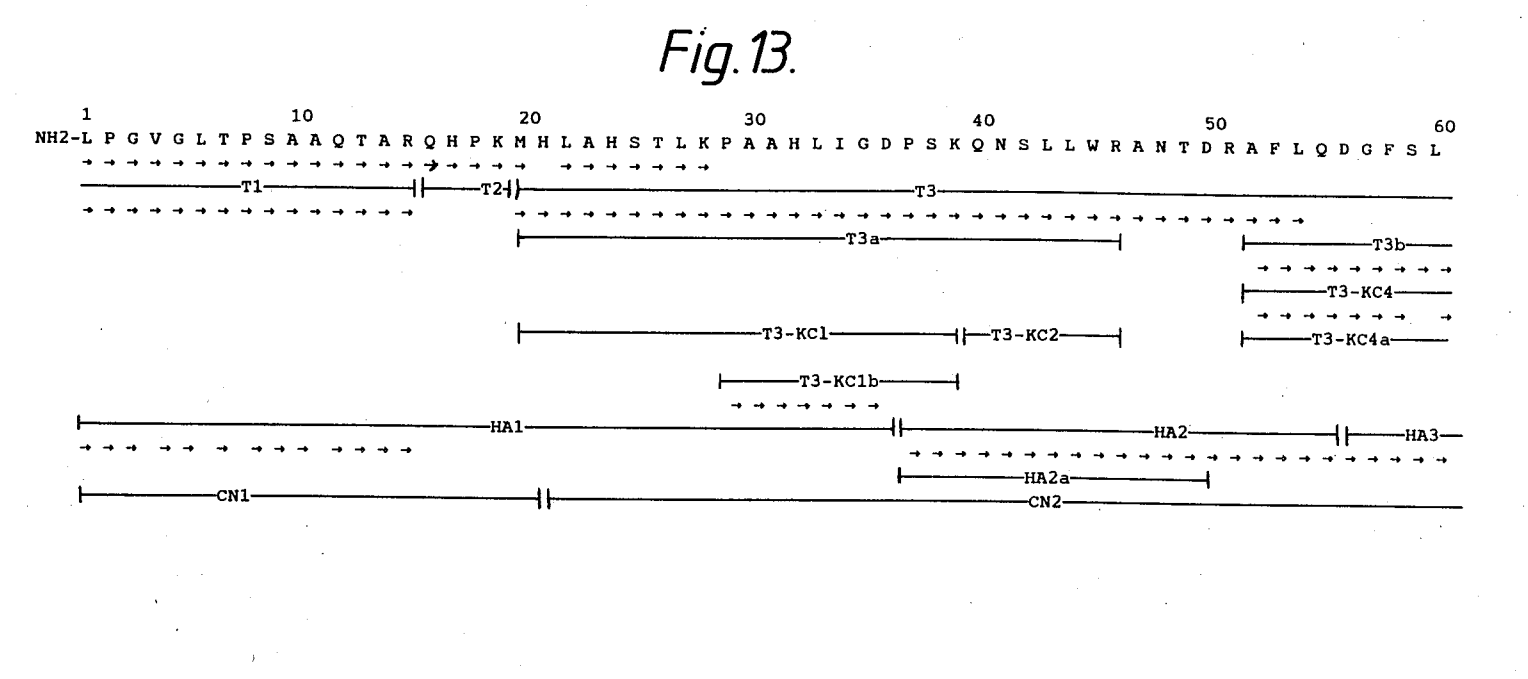

The nomenclature of peptide fragments of lymphotoxin is according to the cleavage procedure used, and they are numbered sequently from the NH$_2$-terminus. FIG. 13 summarizes the cleavage and overlap strategy used for determining the total amino acid sequence applicable in whole or part to both N-terminal species. Solid lines indicate the total length of a given peptide. Forward and backward arrows indicate amino acid sequence by Edman degradation and by carboxypeptidse digestion, respectively. Specific designations are summarized below:

Tryptic peptides of intact lymphotoxin

T1 (1-15), T2 (16-19), T3 (2089), T3a (20-46), T3b (52-89), T4 (90-171), T4a (90-119) and T4b (120-171).

Lysine-C peptidase fragments of T3 peptide

T3-KC1(20-39), T3-KC1b (29-39), T3-KC2 (40-46), T3-KC4 (52-84), T3-KC4a (52-74), T3-KC4b (75-84) and T3-KC5 (85-89).

Acetic acid fragments of intact lymphotoxin HA1 (1-36), HA2 (37-55), HA2a (37-50) and HA3 (57-171).

CnBr fragments of T4 peptide

T4-CN1 (90-120), T4 CN2 (121-133) and T4 CN3 (134-171).

CNBr fragments of intact lymphotoxin

CN1 (1-20), CN2 (21-120), CN3 (121-133) and CN4 (134-171).

Chrmotryptic fragments of T4-CN3 peptide

T4-CN3-CY1 (134-139), T4,CN3-CY2 (140-159), T4-CN3-CY3 (160-165), T4-CN3-CY4 (166-169) and T4-CN3-CY5 (170-171).

The intact 25,000 Da lymphotoxin purified in accordance with this example was cleaved at three major sites when exposed to 5 percent (w/w) trypsin for 24 h. The three tryptic peptides T1, T3 and T4 which were fractionated by high performance liquid chromatography (HPLC) contain the entire sequence except for residues 16-19 (tryptic fragment T2), which was not recovered from HPLC. Tryptic fragments T3 and T4 described here correspond to peptide T1 and T2 respectively reported above. Edman degradation of the intact protein and tryptic fragments T1 and T3 established residues 1 through 41. In a later experiment, a tryptic digest of a larger amount of lymphotoxin (10 nmole) run on HPLC provided a minor fragment T3b which was not completely resolved from fragment T3. Peptides T3 and T3b were sequenced as a mixture through 35 cycles of Edman degradation and the amino acid sequence was extended up to residue 86. The tryptic fragment T3 was further digested with Lysine-C peptidase which generated peptides T3-KC1b, T3-KC4b, T3-KC5 and T3-KC4. This confirmed and extended the sequence to residue 89.

Tryptic fragment T4 of lymphotoxin was sequenced 40 cycles and thereafter the peptide was extracted from the sequencer with 70 percent formic acid. CNBr was added and the reaction was allowed to stand at room temperature for 40 h; then the mixture was reapplied to the sequencer. This resulted in two distinct sequences, which is consistant with the number of methionine residues present as indicated by amino acid composition. Although residues 32-40 of peptide T4 has already been sequenced, cleavage by CNBr at methionine residue 31 allowed these residues to be resequenced and confirmed in the mixture. The yield of valine at residue 32 was eightfold higher than originally seen during the initial sequencing of the intact T4 peptide. This is due to the partial blocking that occurs during the Edman degradation, allowing an accumulation of unsequenced peptide in the cup. In addition to reconfirming a portion of the sequence, cleavage by CNBr enabled 20 new residues to be identified. Further sequencing of the intact T4 peptide would have failed to reveal new sequence information due to the low signal (6 nmole) at cycle 40. Following CNBr cleavage, the yield was increased to 489 pmoles for tyrosine. This procedure should provide useful technique when a peptide is known to contain methionine residues and only a limited amount of material is available. Trypsin digestion of lymphotoxin also provided a fragment T4b which assisted in extending the sequence to residue 135. CNBr digestion of tryptic fragment T4 provided peptide T4-CN3 which extended the sequence to residue 155.

In order to obtain an overlap between peptides T3 and T4, intact lymphotoxin was cleaved with acetic acid and the fragments were separated by HPLC. Peptides HA2 and HA3 which could not be resolved by HPLC were sequenced as a mixture and provided an overlap between tryptic fragments T3 and T4. Carboxyl terminal sequencing of lymphotoxin was carried out on CNBr fragment CN4 and on the intact molecule using carboxypeptidase P. The results indicate that the amino acid sequence at the carboxyl terminus is -Phe-Ala-Leu.

H. References

The bibliography appended thereto, and referenced in the foregoing text is included to enhance the understanding of the invention. The subject matter so referenced is thereby incorporated herein.

BIBLIOGRAPHY

1. Evans, *Cancer Immunology and Immunotherapy* 12, 181 (1982).
2. Holterman, O. A., et al. "Studies on local administration of materials with lymphokine activity to neoplasms involving the skin." In M. A. Fink (ed.) The macorphase in neoplasia. pp 259-261, *Academic Press, New York* (1976).
3. May-Levin, F., et al. *Schweiz. Med. Wsch,* 102:1188 (1972)
4. Papermaster, B. W., et al. *Res. Comm. Chem. Pah. Pharmacol,* 8:413 (1974)
5. Papermaster, B. W., et al. *Clin. Immunol. Immunopathol,* 5:31 (1976)
6. Papermaster, B. W., et al. *Ann. N.Y. Acad. Sci,* 332:451 (1979)
7. Khan, A., et al. *Hematology and Oncology,* 11:128A (1981)
8. Gately, M. K., et al. *Immunol,* 27:B2(1976)
9. Rosenberg, S. A., et al. *J. Immunol,* 110:1623 (1973)
10. Swada, J. I., et al. *Jap. J. Med.,* 46:263 (1976)
11. Williams, T. W., et al. *Cell Immunol,* 6:171 (1973)
12. Evans, C. H., et al. *Cancer Res.,* 35:1035 (1975)
13. Meltzer, M. S., et al. *J. Nat. Cancer Inst.,* 49:1439 (1972)
14. Rundell, J. O., et al. *Immunopharmacology,* 3:9 (1981)
15. Weedon, D. D., et al. *Mayo Clinic Pro.,* 48:556 (1973)
16. Evans, C. H., et al. *Cancer Res.,* 37:898 (1977)
17. Evans, C. H., et al. *Int. J. Cancer,* 27:45 (1981)
18. Klostergaard, J., et al. *Immunol,* 18:1049 (1981)
19. Klostergaard, J., et al. *Mol. Immunol,* 18:455 (1981)
20. Pitchyangkil, et al. *J. of Clinical Hematology and Oncology* 11, 19A (1981)
21. Amino, N., et al. *J. Immunol,* 113:1334 (1974)
22. Russel, S. W., et al. *J. Immunol,* 109:784 (1972)
23. Fuhrer, J. P., et al. "Biologically active Syrian hamster lymphotoxin indicated in high yield on a Waters I-125 Protein HPLC column." (1982) In International symptons on HPLC of Proteins and peptides held in Washington, D.C. - November 16-17th, 1981
24. Klostergaard, J., et al. *Mol. Immunol,* 17:613 (1980)
25. Lisafeld, et al. *Int. Archs. Allergy Appl. Immun.,* 62:59 (1980)
26. Heffes, et al. *J. Immunol,* 14:64 (1975)
27. Laemmli U. K., et al. *Nature,* 227:680 (1970)
28. Merril, C. R., et al. *Anal Biochem,* 110:201 (1981)
29. Kohr, W., et al. *Anal Biochem* (in press)
30. Spofford, B., et al. *J. Immunol,* 112:2111 (1974)
31. Bradford, N. M., et al. *Anal Brochem,* 72:248 (1976)

I claim:

1. A composition suitable for administration as an anti-tumor agent comprising a substantially homogeneous lymphotoxin having a molecular weight by SDS-PAGE of about 25,000 daltons and the amino acid sequence NH$_2$—Leu Pro Gly Val Gly Leu Thr Pro Ser Ala Ala—
Gln Thr Ala Arg Gln His Pro Lys Met His Leu Ala—
His Ser Thr Leu Lys Pro Ala Ala His Leu Ile Gly—
Asp Pro Ser Lys Gln Asn Ser Leu Leu Trp Arg—
Ala Asn Thr Asp Arg Ala Phe Leu Gln Asp Gly—
Phe Ser Leu Ser Asn Asn Ser Leu Leu Val Pro—
Thr Ser Gly Ile Tyr Phe Val Tyr Ser Gln Val—
Val Phe Ser Gly Lys Ala Tyr Ser Pro Lys Ala—
Thr Ser Ser Pro Leu Tyr Leu Ala His Glu Val—
Gln Leu Phe Ser Ser Gln Tyr Pro Phe His Val—
Pro Leu Leu Ser Ser Gln Lys Met Val Tyr Pro—
Gly Leu Gln Glu Pro Trp Leu His Ser Met Tyr—
His Gly Ala Ala Phe Gln Leu Thr Gln Gly Asp—
Gln Leu Ser Thr His Thr Asp Gly Ile Pro His—
Leu Val Leu Ser Pro Ser Thr Val Phe Phe Gly—
Ala Phe Ala Leu to pharmaceutically acceptable derivates prepared from the functional groups on the side chains of amino acids, or the N- or C- terminal groups; to enzymatic or chemically hydrolyzed fragments; to aggregates which are the result of lymphotoxin trimers; or to pharmaceutically acceptable salts, wherein such derivatives, fragments, aggregates and salts maintain the biological activity of mature lymphotoxin and which do not confer toxic properties to the composition; said lymphotoxin having a specific activity of greater than about $10 \times 10^6$ units/mg of protein.

2. The composition of claim 1 wherein the lymphotoxin N-terminal residue is histidyl instead of a leucyl residue.

3. The composition of claim 1 wherein the lymphotoxin has a specific activity of greater than about $50 \times 10^6$ units/mg of protein.

4. The composition of claim 1 wherein the lymphotoxin fragment is a trypsin digest fragment.

5. The composition of claim 1 wherein the aggregate has lymphotoxin a molecular weight of about 64,000 daltons by gel permeation chromatography.

6. The composition of claim 1 which isoelectrically focuses within a pH range of about from 5.5 to 6.5.

7. The composition of claim 1 which has an isoelectric point of about 5.8.

8. The composition of claim 1 wherein the lymphotoxin is a fragment having a molecular weight by SDS-PAGE of about 20,000 daltons and having the sequence His Ser Thr Leu Lys Pro Ala Ala His Leu Ile Gly—
Asp Pro Ser Lys Gln Asn Ser Leu Leu Trp Arg—
Ala Asn Thr Asp Arg Ala Phe Leu Gln Asp Gly—
Phe Ser Leu Ser Asn Asn Ser Leu Leu Val Pro—
Thr Ser Gly Ile Tyr Phe Val Tyr Ser Gln Val—
Val Phe Ser Gly Lys Ala Tyr Ser Pro Lys Ala—
Thr Ser Ser Pro Leu Tyr Leu Ala His Glu Val—
Gln Leu Phe Ser Ser Gln Tyr Pro Phe His Val—
Pro Leu Leu Ser Ser Gln Lys Met Val Tyr Pro—
Gly Leu Gln Glu Pro Trp Leu His Ser Met Tyr—
His Gly Ala Ala Phe Gln Leu Thr Gln Gly Asp—
Gln Leu Ser Thr His Thr Asp Gly Ile Pro His—
Leu Val Leu Ser Pro Ser Thr Val Phe Phe Gly—
Ala Phe Ala Leu 9. A composition suitable for administration as an antitumor agent comprising a substantially homogeneous lymphotoxin having a molecular weight of about 25,000 daltons by SDS-PAGE and the amino acid sequence NH$_2$—Leu Pro Gly Val Gly Leu Thr Pro Ser Ala Ala—
Gln Thr Ala Arg Gln His Pro Lys Met His Leu Ala—
His Ser Thr Leu Lys Pro Ala Ala His Leu Ile Gly—
Asp Pro Ser Lys Gln Asn Ser Leu Leu Trp Arg—
Ala Asn Thr Asp Arg Ala Phe Leu Gln Asp Gly—
Phe Ser Leu Ser Asn Asn Ser Leu Leu Val Pro—
Thr Ser Gly Ile Tyr Phe Val Tyr Ser Gln Val—
Val Phe Ser Gly Lys Ala Tyr Ser Pro Lys Ala—
Thr Ser Ser Pro Leu Tyr Leu Ala His Glu Val—
Gln Leu Phe Ser Ser Gln Tyr Pro Phe His Val—
Pro Leu Leu Ser Ser Gln Lys Met Val Tyr Pro—
Gly Leu Gln Glu Pro Trp Leu His Ser Met Tyr—
His Gly Ala Ala Phe Gln Leu Thr Gln Gly Asp—
Gln Leu Ser Thr His Thr Asp Gly Ile Pro His—
Leu Val Leu Ser Pro Ser Thr Val Phe Phe Gly—
Ala Phe Ala Leu, to pharmaceutically acceptable derivatives prepared from the functional groups on the side chains of amino acids, or the N- or C-terminal groups; to enzymatic or chemically hydrolyzed fragments; to aggregates which are the result of lymphotoxin trimers; or to pharmaceutically acceptable salts, wherein such derivatives, fragments, aggregates and salts maintain the biological activity of mature lymphotoxin and which do not confer toxic properties to the composition;

10. The composition of claim 9 which isoelectrically focuses within a pH range of about from 5.5 to 6.5.

11. A composition suitable for administration as an anti-tumor agent comprising a substantially homogeneous lymphotoxin having the amino acid sequence

```
NH2—Leu Pro Gly Val Gly Leu Thr Pro Ser Ala Ala—
Gln Thr Ala Arg Gln His Pro Lys Met His Leu Ala—
His Ser Thr Leu Lys Pro Ala Ala His Leu Ile Gly—
Asp Pro Ser Lys Gln Asn Ser Leu Leu Trp Arg—
Ala Asn Thr Asp Arg Ala Phe Leu Gln Asp Gly—
Phe Ser Leu Ser Asn Asn Ser Leu Leu Val Pro—
Thr Ser Gly Ile Tyr Phe Val Tyr Ser Gln Val—
Val Phe Ser Gly Lys Ala Tyr Ser Pro Lys Ala—
Thr Ser Ser Pro Leu Tyr Leu Ala His Glu Val—
Gln Leu Phe Ser Ser Gln Tyr Pro Phe His Val—
Pro Leu Leu Ser Ser Gln Lys Met Val Tyr Pro—
Gly Leu Gln Glu Pro Trp Leu His Ser Met Tyr—
His Gly Ala Ala Phe Gln Leu Thr Gln Gly Asp—
Gln Leu Ser Thr His Thr Asp Gly Ile Pro His—
Leu Val Leu Ser Pro Ser Thr Val Phe Phe Gly—
Ala Phe Ala Leu,
``` to pharmaceutically acceptable derivatives prepared from the functional groups on the side chains of amino acids, or the N- or C-terminal groups; to enzymatic or chemically hydrolyzed fragments; to aggregates which are the result of lymphotoxin trimers; or to pharmaceutically acceptable salts, wherein such derivatives, fragments, aggregates and salts maintain the biological activity of mature lymphotoxin and which do not confer toxic properties to the composition; said lymphotoxin having a specific activity of greater than about $10 \times 10^6$ units/mg of protein, a molecular weight by SDS-PAGE of about 25,000 daltons and an isoelectric point of about 5.8.

12. A composition suitable for administration as an anti-tumor agent comprising a substantially homogeneous lymphotoxin having the amino acid sequence

```
His Ser Thr Leu Lys Pro Ala Ala His Leu Ile Gly—
Asp Pro Ser Lys Gln Asn Ser Leu Leu Trp Arg—
Ala Asn Thr Asp Arg Ala Phe Leu Gln Asp Gly—
Phe Ser Leu Ser Asn Asn Ser Leu Leu Val Pro—
Thr Ser Gly Ile Tyr Phe Val Tyr Ser Gln Val—
Val Phe Ser Gly Lys Ala Tyr Ser Pro Lys Ala—
Thr Ser Ser Pro Leu Tyr Leu Ala His Glu Val—
Gln Leu Phe Ser Ser Gln Tyr Pro Phe His Val—
Pro Leu Leu Ser Ser Gln Lys Met Val Tyr Pro—
Gly Leu Gln Glu Pro Trp Leu His Ser Met Tyr—
His Gly Ala Ala Phe Gln Leu Thr Gln Gly Asp—
Gln Leu Ser Thr His Thr Asp Gly Ile Pro His—
Leu Val Leu Ser Pro Ser Thr Val Phe Phe Gly—
Ala Phe Ala Leu,
``` to pharmaceutically acceptable derivatives prepared from the functional groups on the side chains of amino acids, or the N- or C-terminal groups; to enzymatic or chemically hydrolyzed fragments; to aggregates which are the result of lymphotoxin trimers; or to pharmaceutically acceptable salts, wherein such derivatives, fragments, aggregates and salts maintain the biological activity of mature lymphotoxin and which do not confer toxic properties to the composition; said lymphotoxin having a specific activity of greater than about $10 \times 10^6$ units/mg of protein, a molecular weight by SDS-PAGE of about 20,000 daltons and which isoelectrically focuses within a pH range of about from 5.5 to 6.5.

13. A pharmaceutical composition useful for treating tumors in humans which comprises a therapeutically effective amount of the composition of any one of claims 1, 9, 11, or 12 in admixture with a pharmaceutically acceptable excipient.

14. A process for preparing human lymphotoxin having a molecular weight by SDS-PAGE of about 25,000 daltons and the amino acid sequence

```
NH2—Leu Pro Gly Val Gly Leu Thr Pro Ser Ala Ala—
Gln Thr Ala Arg Gln His Pro Lys Met His Leu Ala—
His Ser Thr Leu Lys Pro Ala Ala His Leu Ile Gly—
Asp Pro Ser Lys Gln Asn Ser Leu Leu Trp Arg—
Ala Asn Thr Asp Arg Ala Phe Leu Gln Asp Gly—
Phe Ser Leu Ser Asn Asn Ser Leu Leu Val Pro—
Thr Ser Gly Ile Tyr Phe Val Tyr Ser Gln Val—
Val Phe Ser Gly Lys Ala Tyr Ser Pro Lys Ala—
Thr Ser Ser Pro Leu Tyr Leu Ala His Glu Val—
Gln Leu Phe Ser Ser Gln Tyr Pro Phe His Val—
Pro Leu Leu Ser Ser Gln Lys Met Val Tyr Pro—
Gly Leu Gln Glu Pro Trp Leu His Ser Met Tyr—
His Gly Ala Ala Phe Gln Leu Thr Gln Gly Asp—
Gln Leu Ser Thr His Thr Asp Gly Ile Pro His—
Leu Val Leu Ser Pro Ser Thr Val Phe Phe Gly—
Ala Phe Ala Leu,
``` and fragments thereof, which process comprises
(a) obtaining an extract, supernatant or filtrate from a cell culture which produces lymphotoxin;
(b) treating said extract, supernatant, or filtrate with a lentil lectin adsorbent; and
(c) selectively eluting the lymphotoxin from the adsorbent.

15. The process of claim 14 which includes, before step (b), the additional step of isoelectric focusing.

16. The process of claim 14 which includes, before step (b), the additional step of DEAE-cellulose chromatography.

17. The process of claim 15 which includes, before or after the step of isoelectric focusing, the additional step of DEAE-cellulose chromatography.

18. The process of claim 14 where the lymphotoxin is human and the cell culture is a human lymphoblastoid cell line.

19. The process of claim 18 wherein the cell line is RPMI 1788.

20. The process of any one of claim 1 through 6 wherein the cell culture has been grown in serum-free medium.

21. The process of claim 14 wherein a proteolytic enzyme inhibitor is present during the process.

22. The process of claim 21 wherein the inhibitor is added to the extract, supernatant or filtrate.

23. The process of claim 14 wherein a microbial growth inhibitor is present during the process.

24. The process of claim 14 further comprising first treating the extract, supernatant, or filtrate with controlled pore glass and selectively eluting the lymphotoxin from the controlled pore glass.

25. The process of claim 14 wherein the lymphotoxin in step (c) is obtained by selectively eluting with a solution containing mannose or galactose.

26. A process for preparing lymphotoxin, which process comprises:
(a) culturing a human lymphoid cell line in a culture medium;
(b) inducing lymphotoxin by the inclusion of phorbol myristate acetate in the culture medium;
(c) obtaining an extract, supernatant or filtrate from the culture medium of step (b);
(d) treating the extract, supernatant or filtrate of step (c) with controlled pore glass;

(e) eluting lymphotoxin from the controlled pore glass of step (d);
(f) treating the eluate from step (e) with lentil lectin adsorbent; and
(g) eluting the lymphotoxin from the lentil lectin adsorbent.

27. A process for preparing lymphotoxin, which process comprises:
(a) obtaining an extract, supernatant or filtrate from a cell culture which produces lymphotoxin;
(b) treating said extract, supernatant, or filtrate with a silicate in order to adsorb the lymphotoxin; and
(c) selectively eluting the lymphotoxin from the silicate.

28. A process for preparing lymphotoxin, which process comprises adding a proteolytic enzyme inhibitor to a lymphotoxin-containing extract, supernatant or filtrate so as to inhibit a proteolytic enzyme in the extract, supernatant or filtrate capable of proteolytically cleaving lymphotoxin.

* * * * *